(12) United States Patent
Swensgard et al.

(10) Patent No.: US 8,851,354 B2
(45) Date of Patent: Oct. 7, 2014

(54) SURGICAL CUTTING INSTRUMENT THAT ANALYZES TISSUE THICKNESS

(75) Inventors: Brett E. Swensgard, West Chester, OH (US); Bret W. Smith, Kings Mills, OH (US); Ryan J. Laurent, Liberty Township, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 615 days.

(21) Appl. No.: 12/647,134

(22) Filed: Dec. 24, 2009

(65) Prior Publication Data
US 2011/0155781 A1 Jun. 30, 2011

(51) Int. Cl.
*A61B 17/04* (2006.01)
*A61B 17/10* (2006.01)
*A61B 17/00* (2006.01)
*A61B 19/00* (2006.01)
*A61B 17/072* (2006.01)
*A61B 18/14* (2006.01)
*A61B 17/32* (2006.01)

(52) U.S. Cl.
CPC . *A61B 17/07207* (2013.01); *A61B 2017/00734* (2013.01); *A61B 2019/461* (2013.01); *A61B 2017/07214* (2013.01); *A61B 2017/00398* (2013.01); *A61B 2017/00022* (2013.01); *A61B 2017/0023* (2013.01); *A61B 18/1445* (2013.01); *A61B 2017/320052* (2013.01)
USPC ............................................... 227/176.1

(58) Field of Classification Search
USPC ............. 227/175.1–182.1; 606/139, 142, 143
See application file for complete search history.

(56) References Cited

U.S. PATENT DOCUMENTS

| 2,853,074 | A | | 9/1958 | Olson |
| 3,551,987 | A | | 1/1971 | Wilkinson |
| 4,429,695 | A | | 2/1984 | Green |
| 4,506,671 | A | | 3/1985 | Green |
| 4,619,262 | A | | 10/1986 | Taylor |
| 4,809,695 | A | | 3/1989 | Gwathmey et al. |
| 4,844,068 | A | | 7/1989 | Arata et al. |
| 5,383,880 | A | * | 1/1995 | Hooven ......................... 606/142 |
| 5,395,033 | A | * | 3/1995 | Byrne et al. ................. 227/175.1 |

(Continued)

FOREIGN PATENT DOCUMENTS

| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Robert Long

(57) ABSTRACT

A surgical instrument with a tissue-clamping end effector, where actuation of the instrument is locked out when the thickness of the tissue clamped in the end effector is not within a specified thickness range. The end effector may comprise a tissue thickness module that senses the thickness of the tissue clamped in the end effector. The surgical instrument also comprises a control circuit in communication with the tissue thickness module. The control circuit prevents actuation of a working portion of the end effector when the thickness of the tissue clamped in the end effector is not within the specified thickness range.

21 Claims, 12 Drawing Sheets

(56) References Cited

U.S. PATENT DOCUMENTS

| | | | |
|---|---|---|---|
| 5,403,312 A | 4/1995 | Yates et al. | |
| 5,405,072 A | 4/1995 | Zlock et al. | |
| 5,413,272 A | 5/1995 | Green et al. | |
| 5,415,334 A | 5/1995 | Williamson, IV et al. | |
| 5,417,361 A | 5/1995 | Williamson, IV | |
| 5,480,089 A | 1/1996 | Blewett | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,505,363 A | 4/1996 | Green et al. | |
| 5,509,596 A | 4/1996 | Green et al. | |
| 5,518,163 A | 5/1996 | Hooven | |
| 5,529,235 A | 6/1996 | Boiarski et al. | |
| 5,533,661 A | 7/1996 | Main et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,553,765 A | 9/1996 | Knodel et al. | |
| 5,560,530 A | 10/1996 | Bolanos et al. | |
| 5,560,532 A | 10/1996 | DeFonzo et al. | |
| 5,562,239 A * | 10/1996 | Boiarski et al. | 227/175.2 |
| 5,562,241 A | 10/1996 | Knodel et al. | |
| 5,564,615 A | 10/1996 | Bishop et al. | |
| 5,577,654 A | 11/1996 | Bishop | |
| 5,580,067 A | 12/1996 | Hamblin et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,601,224 A | 2/1997 | Bishop et al. | |
| 5,603,443 A | 2/1997 | Clark et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |
| 5,636,780 A | 6/1997 | Green et al. | |
| 5,639,008 A | 6/1997 | Gallagher et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,685,474 A | 11/1997 | Seeber | |
| 5,688,270 A | 11/1997 | Yates et al. | |
| 5,690,269 A | 11/1997 | Bolanos et al. | |
| 5,692,668 A | 12/1997 | Schulze et al. | |
| 5,697,543 A | 12/1997 | Burdorff | |
| 5,704,534 A | 1/1998 | Huitema et al. | |
| 5,709,680 A | 1/1998 | Yates et al. | |
| 5,711,472 A | 1/1998 | Bryan | |
| 5,713,505 A | 2/1998 | Huitema | |
| 5,715,987 A | 2/1998 | Kelley et al. | |
| 5,718,360 A | 2/1998 | Green et al. | |
| 5,732,871 A | 3/1998 | Clark et al. | |
| 5,732,872 A | 3/1998 | Bolduc et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,256 A | 6/1998 | Mastri et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,397 A | 7/1998 | Koukline | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,799,857 A | 9/1998 | Robertson et al. | |
| 5,820,009 A | 10/1998 | Melling et al. | |
| 5,826,776 A | 10/1998 | Schulze et al. | |
| 5,829,662 A | 11/1998 | Allen et al. | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,871,135 A | 2/1999 | Williamson, IV et al. | |
| 5,901,895 A | 5/1999 | Heaton et al. | |
| 5,911,353 A | 6/1999 | Bolanos et al. | |
| 5,915,616 A | 6/1999 | Viola et al. | |
| 5,941,442 A | 8/1999 | Geiste et al. | |
| 5,951,581 A * | 9/1999 | Saadat et al. | 606/170 |
| 5,954,259 A | 9/1999 | Viola et al. | |
| 6,010,054 A | 1/2000 | Johnson et al. | |
| 6,032,849 A | 3/2000 | Mastri et al. | |
| 6,053,390 A | 4/2000 | Green et al. | |
| 6,102,271 A | 8/2000 | Longo et al. | |
| 6,119,913 A | 9/2000 | Adams et al. | |
| 6,126,058 A | 10/2000 | Adams et al. | |
| 6,193,129 B1 | 2/2001 | Bittner et al. | |
| 6,202,914 B1 | 3/2001 | Geiste et al. | |
| 6,224,617 B1 * | 5/2001 | Saadat et al. | 606/170 |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,330,965 B1 | 12/2001 | Milliman et al. | |
| 6,488,196 B1 | 12/2002 | Fenton, Jr. | |
| 6,488,197 B1 | 12/2002 | Whitman | |
| 6,491,201 B1 | 12/2002 | Whitman | |
| 6,505,768 B2 | 1/2003 | Whitman | |
| 6,578,751 B2 | 6/2003 | Hartwick | |
| 6,588,643 B2 | 7/2003 | Bolduc et al. | |
| 6,601,749 B2 | 8/2003 | Sullivan et al. | |
| 6,619,529 B2 | 9/2003 | Green et al. | |
| 6,629,630 B2 | 10/2003 | Adams | |
| 6,644,532 B2 | 11/2003 | Green et al. | |
| 6,681,978 B2 | 1/2004 | Geiste et al. | |
| 6,681,979 B2 | 1/2004 | Whitman | |
| 6,695,199 B2 | 2/2004 | Whitman | |
| 6,698,643 B2 | 3/2004 | Whitman | |
| 6,716,233 B1 * | 4/2004 | Whitman | 606/219 |
| 6,755,338 B2 | 6/2004 | Hahnen et al. | |
| 6,769,594 B2 | 8/2004 | Orban, III | |
| 6,786,382 B1 | 9/2004 | Hoffman | |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,830,174 B2 | 12/2004 | Hillstead et al. | |
| 6,843,403 B2 | 1/2005 | Whitman | |
| RE38,708 E | 3/2005 | Bolanos et al. | |
| 6,874,669 B2 | 4/2005 | Adams et al. | |
| 6,877,647 B2 | 4/2005 | Green et al. | |
| 6,905,057 B2 | 6/2005 | Swayze et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |

(56) References Cited

U.S. PATENT DOCUMENTS

| | | | |
|---|---|---|---|
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,070,083 B2 | 7/2006 | Jankowski |
| 7,080,769 B2 | 7/2006 | Vresh et al. |
| 7,083,075 B2 | 8/2006 | Swayze et al. |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,159,750 B2 | 1/2007 | Racenet et al. |
| 7,168,604 B2 | 1/2007 | Milliman et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et |
| 7,213,736 B2 | 5/2007 | Wales et al. |
| 7,225,964 B2 | 6/2007 | Mastri et al. |
| 7,234,624 B2 | 6/2007 | Gresham et al. |
| 7,237,708 B1 | 7/2007 | Guy et al. |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,286,850 B2 | 10/2007 | Frielink et al. |
| 7,296,724 B2 | 11/2007 | Green et al. |
| 7,303,106 B2 * | 12/2007 | Milliman et al. ........... 227/175.1 |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,481,349 B2 | 1/2009 | Holsten et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,564 B2 | 6/2009 | Boudreaux |
| 7,556,186 B2 | 7/2009 | Milliman |
| 7,559,450 B2 | 7/2009 | Wales et al. |
| 7,568,603 B2 | 8/2009 | Shelton, IV et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,631,793 B2 | 12/2009 | Rethy et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,717,312 B2 * | 5/2010 | Beetel ........................ 227/175.1 |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,909,221 B2 | 3/2011 | Viola et al. |
| 7,922,063 B2 * | 4/2011 | Zemlok et al. ............. 227/176.1 |
| 7,950,560 B2 | 5/2011 | Zemlok et al. |
| 8,011,551 B2 | 9/2011 | Marczyk et al. |
| D650,074 S | 12/2011 | Hunt et al. |
| 8,267,924 B2 * | 9/2012 | Zemlok et al. ..................... 606/1 |
| 8,506,557 B2 * | 8/2013 | Zemlok et al. ..................... 606/1 |

(56) References Cited

U.S. PATENT DOCUMENTS

| | | | |
|---|---|---|---|
| 8,540,733 B2 * | 9/2013 | Whitman et al. | 606/139 |
| 2002/0117534 A1 | 8/2002 | Green et al. | |
| 2004/0094597 A1 | 5/2004 | Whitman et al. | |
| 2004/0108357 A1 | 6/2004 | Milliman et al. | |
| 2004/0164123 A1 | 8/2004 | Racenet et al. | |
| 2004/0173659 A1 | 9/2004 | Green et al. | |
| 2004/0222268 A1 | 11/2004 | Bilotti et al. | |
| 2004/0232201 A1 | 11/2004 | Wenchell et al. | |
| 2005/0103819 A1 | 5/2005 | Racenet et al. | |
| 2005/0131390 A1 | 6/2005 | Heinrich et al. | |
| 2005/0145675 A1 | 7/2005 | Hartwick et al. | |
| 2005/0184121 A1 | 8/2005 | Heinrich | |
| 2005/0189397 A1 | 9/2005 | Jankowski | |
| 2005/0263563 A1 | 12/2005 | Racenet et al. | |
| 2005/0274768 A1 | 12/2005 | Cummins et al. | |
| 2006/0011699 A1 | 1/2006 | Olson et al. | |
| 2006/0025811 A1 | 2/2006 | Shelton, IV | |
| 2006/0049229 A1 | 3/2006 | Milliman et al. | |
| 2006/0108393 A1 | 5/2006 | Heinrich et al. | |
| 2006/0180634 A1 | 8/2006 | Shelton, IV et al. | |
| 2006/0212069 A1 | 9/2006 | Shelton, IV | |
| 2006/0226196 A1 | 10/2006 | Hueil et al. | |
| 2006/0273135 A1 * | 12/2006 | Beetel | 227/175.1 |
| 2006/0278680 A1 | 12/2006 | Viola et al. | |
| 2006/0278681 A1 | 12/2006 | Viola et al. | |
| 2006/0289602 A1 | 12/2006 | Wales et al. | |
| 2007/0023476 A1 | 2/2007 | Whitman et al. | |
| 2007/0023477 A1 | 2/2007 | Whitman et al. | |
| 2007/0034668 A1 | 2/2007 | Holsten et al. | |
| 2007/0084897 A1 | 4/2007 | Shelton, IV et al. | |
| 2007/0102472 A1 | 5/2007 | Shelton, IV | |
| 2007/0106317 A1 | 5/2007 | Shelton, IV et al. | |
| 2007/0114261 A1 | 5/2007 | Ortiz et al. | |
| 2007/0170225 A1 | 7/2007 | Shelton, IV et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175953 A1 | 8/2007 | Shelton, IV et al. | |
| 2007/0175955 A1 | 8/2007 | Shelton, IV et al. | |
| 2007/0179408 A1 * | 8/2007 | Soltz | 600/587 |
| 2007/0181632 A1 | 8/2007 | Milliman | |
| 2007/0194079 A1 | 8/2007 | Hueil et al. | |
| 2007/0194081 A1 | 8/2007 | Hueil et al. | |
| 2007/0194082 A1 | 8/2007 | Morgan et al. | |
| 2007/0221700 A1 | 9/2007 | Ortiz et al. | |
| 2007/0221701 A1 | 9/2007 | Ortiz et al. | |
| 2007/0225562 A1 | 9/2007 | Spivey et al. | |
| 2007/0246505 A1 | 10/2007 | Pace-Floridia et al. | |
| 2007/0295780 A1 | 12/2007 | Shelton et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0035701 A1 | 2/2008 | Racenet et al. | |
| 2008/0041917 A1 | 2/2008 | Racenet et al. | |
| 2008/0078800 A1 | 4/2008 | Hess et al. | |
| 2008/0078802 A1 | 4/2008 | Hess et al. | |
| 2008/0078803 A1 | 4/2008 | Shelton et al. | |
| 2008/0078804 A1 | 4/2008 | Shelton et al. | |
| 2008/0078806 A1 | 4/2008 | Omaits et al. | |
| 2008/0078807 A1 | 4/2008 | Hess et al. | |
| 2008/0078808 A1 | 4/2008 | Hess et al. | |
| 2008/0082115 A1 | 4/2008 | Morgan et al. | |
| 2008/0082125 A1 | 4/2008 | Murray et al. | |
| 2008/0082126 A1 | 4/2008 | Murray et al. | |
| 2008/0083813 A1 | 4/2008 | Zemlok et al. | |
| 2008/0167522 A1 | 7/2008 | Giordano et al. | |
| 2008/0167644 A1 | 7/2008 | Shelton et al. | |
| 2008/0167671 A1 | 7/2008 | Giordano et al. | |
| 2008/0167672 A1 | 7/2008 | Giordano et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0197167 A1 | 8/2008 | Viola et al. | |
| 2008/0210738 A1 | 9/2008 | Shelton et al. | |
| 2008/0237296 A1 | 10/2008 | Boudreaux et al. | |
| 2008/0251568 A1 | 10/2008 | Zemlok et al. | |
| 2008/0255418 A1 * | 10/2008 | Zemlok et al. | 600/118 |
| 2008/0283570 A1 | 11/2008 | Boyden et al. | |
| 2008/0283577 A1 * | 11/2008 | Boyden et al. | 227/181.1 |
| 2008/0290134 A1 | 11/2008 | Bettuchi et al. | |
| 2008/0296346 A1 | 12/2008 | Shelton, IV et al. | |
| 2008/0300580 A1 | 12/2008 | Shelton, IV et al. | |
| 2008/0300613 A1 | 12/2008 | Shelton, IV et al. | |
| 2008/0308602 A1 | 12/2008 | Timm et al. | |
| 2008/0308603 A1 | 12/2008 | Shelton, Jr. et al. | |
| 2008/0308608 A1 | 12/2008 | Prommersberger | |
| 2008/0314957 A1 | 12/2008 | Boudreaux | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001124 A1 | 1/2009 | Hess et al. | |
| 2009/0001130 A1 | 1/2009 | Hess et al. | |
| 2009/0005807 A1 | 1/2009 | Hess et al. | |
| 2009/0005808 A1 | 1/2009 | Hess et al. | |
| 2009/0005809 A1 | 1/2009 | Hess et al. | |
| 2009/0012556 A1 | 1/2009 | Boudreaux et al. | |
| 2009/0057369 A1 | 3/2009 | Smith et al. | |
| 2009/0076534 A1 | 3/2009 | Shelton, IV et al. | |
| 2009/0090763 A1 * | 4/2009 | Zemlok et al. | 227/175.2 |
| 2009/0108048 A1 | 4/2009 | Zemlok et al. | |
| 2009/0114701 A1 | 5/2009 | Zemlok et al. | |
| 2009/0149871 A9 | 6/2009 | Kagan et al. | |
| 2009/0206125 A1 | 8/2009 | Huitema et al. | |
| 2009/0206126 A1 | 8/2009 | Huitema et al. | |
| 2009/0206131 A1 | 8/2009 | Weisenburgh, II et al. | |
| 2009/0206132 A1 | 8/2009 | Hueil et al. | |
| 2009/0206133 A1 | 8/2009 | Morgan et al. | |
| 2009/0206137 A1 | 8/2009 | Hall et al. | |
| 2009/0206138 A1 | 8/2009 | Smith et al. | |
| 2009/0206139 A1 | 8/2009 | Hall et al. | |
| 2009/0206140 A1 | 8/2009 | Scheib et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0206144 A1 | 8/2009 | Doll et al. | |
| 2009/0209946 A1 | 8/2009 | Swayze et al. | |
| 2009/0209979 A1 | 8/2009 | Yates et al. | |
| 2009/0209990 A1 | 8/2009 | Yates et al. | |
| 2009/0218384 A1 | 9/2009 | Aranyi | |
| 2009/0242610 A1 | 10/2009 | Shelton, IV et al. | |
| 2009/0255974 A1 | 10/2009 | Viola | |
| 2009/0255975 A1 | 10/2009 | Zemlok et al. | |
| 2009/0255976 A1 | 10/2009 | Marczyk et al. | |
| 2009/0255977 A1 | 10/2009 | Zemlok | |
| 2009/0255978 A1 | 10/2009 | Viola et al. | |
| 2009/0289096 A1 | 11/2009 | Shelton, IV et al. | |
| 2010/0001036 A1 | 1/2010 | Marczyk et al. | |
| 2010/0032470 A1 | 2/2010 | Hess et al. | |
| 2010/0065605 A1 | 3/2010 | Shelton, VI et al. | |
| 2010/0069942 A1 | 3/2010 | Shelton, IV | |
| 2010/0072252 A1 | 3/2010 | Baxter, III et al. | |
| 2010/0072256 A1 | 3/2010 | Baxter, III et al. | |
| 2010/0076474 A1 | 3/2010 | Yates et al. | |
| 2010/0076475 A1 | 3/2010 | Yates et al. | |
| 2010/0089970 A1 | 4/2010 | Smith et al. | |
| 2010/0089972 A1 * | 4/2010 | Marczyk | 227/178.1 |
| 2010/0089974 A1 | 4/2010 | Shelton, IV | |
| 2010/0096435 A1 | 4/2010 | Fuchs et al. | |
| 2010/0108741 A1 | 5/2010 | Hessler et al. | |
| 2010/0127042 A1 | 5/2010 | Shelton, IV | |
| 2010/0133317 A1 | 6/2010 | Shelton, IV et al. | |
| 2010/0133318 A1 | 6/2010 | Boudreaux | |
| 2010/0163598 A1 | 7/2010 | Belzer | |
| 2010/0179382 A1 | 7/2010 | Shelton, IV et al. | |
| 2010/0181364 A1 | 7/2010 | Shelton, IV et al. | |
| 2010/0193566 A1 | 8/2010 | Scheib et al. | |
| 2010/0193567 A1 | 8/2010 | Scheib et al. | |
| 2010/0193568 A1 | 8/2010 | Scheib et al. | |
| 2010/0193569 A1 | 8/2010 | Yates et al. | |
| 2010/0198220 A1 | 8/2010 | Boudreaux et al. | |

(56) References Cited

U.S. PATENT DOCUMENTS

| | | |
|---|---|---|
| 2010/0200637 A1* | 8/2010 | Beetel .................. 227/175.1 |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1* | 11/2010 | Boyden et al. ............. 227/175.1 |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1* | 1/2011 | Zemlok et al. ............. 227/175.1 |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |

FOREIGN PATENT DOCUMENTS

| | | |
|---|---|---|
| CA | 2514274 A1 | 1/2006 |
| CN | 1868411 A | 11/2006 |
| CN | 1915180 A | 2/2007 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |

(56) References Cited

FOREIGN PATENT DOCUMENTS

| | | |
|---|---|---|
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1330201 B1 | 6/2008 |
| EP | 1702568 B1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 1759640 B1 | 12/2008 |
| EP | 2000102 A2 | 12/2008 |
| EP | 1736104 B1 | 3/2009 |
| EP | 1749486 B1 | 3/2009 |
| EP | 1721576 B1 | 4/2009 |
| EP | 1733686 B1 | 4/2009 |
| EP | 1745748 B1 | 8/2009 |
| EP | 2090256 A2 | 8/2009 |
| EP | 1813208 B1 | 11/2009 |
| EP | 1607050 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1785098 B1 | 10/2010 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |

(56) References Cited

FOREIGN PATENT DOCUMENTS

| | | | |
|---|---|---|---|
| GB | 1217159 | A | 12/1970 |
| GB | 1339394 | A | 12/1973 |
| GB | 2109241 | A | 6/1983 |
| GB | 2272159 | A | 5/1994 |
| GB | 2284242 | A | 5/1995 |
| GB | 2336214 | A | 10/1999 |
| GB | 2425903 | A | 11/2006 |
| JP | 6007357 | A | 1/1994 |
| JP | 7051273 | A | 2/1995 |
| JP | 8033641 | A | 2/1996 |
| JP | 8229050 | A | 9/1996 |
| JP | 2000033071 | A | 2/2000 |
| JP | 2000171730 | A | 6/2000 |
| JP | 2000287987 | A | 10/2000 |
| JP | 2000325303 | A | 11/2000 |
| JP | 2001286477 | A | 10/2001 |
| JP | 2002143078 | A | 5/2002 |
| JP | 2002369820 | A | 12/2002 |
| JP | 2005505322 | T | 2/2005 |
| JP | 2005103293 | A | 4/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005152416 | A | 6/2005 |
| JP | 2006-281405 | A | 10/2006 |
| RU | 2008830 | C1 | 3/1994 |
| RU | 2187249 | C2 | 8/2002 |
| RU | 2225170 | C2 | 3/2004 |
| SU | 189517 | A | 1/1967 |
| SU | 328636 | A | 9/1972 |
| SU | 886900 | A1 | 12/1981 |
| SU | 1009439 | A | 4/1983 |
| SU | 1333319 | A2 | 8/1987 |
| SU | 1377053 | A1 | 2/1988 |
| SU | 1561964 | A1 | 5/1990 |
| SU | 1722476 | A1 | 3/1992 |
| WO | WO 91/15157 | A1 | 10/1991 |
| WO | WO 92/20295 | A1 | 11/1992 |
| WO | WO 92/21300 | A1 | 12/1992 |
| WO | WO 93/08755 | A1 | 5/1993 |
| WO | WO 93/13718 | A1 | 7/1993 |
| WO | WO 93/14690 | A1 | 8/1993 |
| WO | WO 93/15648 | A1 | 8/1993 |
| WO | WO 93/15850 | A1 | 8/1993 |
| WO | WO 93/19681 | A1 | 10/1993 |
| WO | WO 94/00060 | A1 | 1/1994 |
| WO | WO 94/11057 | A1 | 5/1994 |
| WO | WO 94/12108 | A1 | 6/1994 |
| WO | WO 94/18893 | A1 | 9/1994 |
| WO | WO 94/22378 | A1 | 10/1994 |
| WO | WO 94/23659 | A1 | 10/1994 |
| WO | WO 95/02369 | A1 | 1/1995 |
| WO | WO 95/03743 | A1 | 2/1995 |
| WO | WO 95/06817 | A1 | 3/1995 |
| WO | WO 95/09576 | A1 | 4/1995 |
| WO | WO 95/09577 | A1 | 4/1995 |
| WO | WO 95/14436 | A1 | 6/1995 |
| WO | WO 95/17855 | A1 | 7/1995 |
| WO | WO 95/18383 | A1 | 7/1995 |
| WO | WO 95/18572 | A1 | 7/1995 |
| WO | WO 95/19739 | A1 | 7/1995 |
| WO | WO 95/20360 | A1 | 8/1995 |
| WO | WO 95/23557 | A1 | 9/1995 |
| WO | WO 95/24865 | A1 | 9/1995 |
| WO | WO 95/25471 | A3 | 9/1995 |
| WO | WO 95/26562 | A1 | 10/1995 |
| WO | WO 95/29639 | A1 | 11/1995 |
| WO | WO 96/04858 | A1 | 2/1996 |
| WO | WO 96/19151 | A1 | 6/1996 |
| WO | WO 96/19152 | A1 | 6/1996 |
| WO | WO 96/20652 | A1 | 7/1996 |
| WO | WO 96/21119 | A1 | 7/1996 |
| WO | WO 96/22055 | A1 | 7/1996 |
| WO | WO 96/23448 | A1 | 8/1996 |
| WO | WO 96/24301 | A1 | 8/1996 |
| WO | WO 96/27337 | A1 | 9/1996 |
| WO | WO 96/31155 | A1 | 10/1996 |
| WO | WO 96/35464 | A1 | 11/1996 |
| WO | WO 96/39085 | A1 | 12/1996 |
| WO | WO 96/39086 | A1 | 12/1996 |
| WO | WO 96/39087 | A1 | 12/1996 |
| WO | WO 96/39088 | A1 | 12/1996 |
| WO | WO 96/39089 | A1 | 12/1996 |
| WO | WO 97/00646 | A1 | 1/1997 |
| WO | WO 97/00647 | A1 | 1/1997 |
| WO | WO 97/06582 | A1 | 2/1997 |
| WO | WO 97/10763 | A1 | 3/1997 |
| WO | WO 97/10764 | A1 | 3/1997 |
| WO | WO 97/11648 | A2 | 4/1997 |
| WO | WO 97/11649 | A1 | 4/1997 |
| WO | WO 97/15237 | A1 | 5/1997 |
| WO | WO 97/24073 | A1 | 7/1997 |
| WO | WO 97/24993 | A1 | 7/1997 |
| WO | WO 97/30644 | A1 | 8/1997 |
| WO | WO 97/34533 | A1 | 9/1997 |
| WO | WO 97/37598 | A1 | 10/1997 |
| WO | WO 97/39688 | A2 | 10/1997 |
| WO | WO 98/17180 | A1 | 4/1998 |
| WO | WO 98/27880 | A1 | 7/1998 |
| WO | WO 98/30153 | A1 | 7/1998 |
| WO | WO 98/47436 | A1 | 10/1998 |
| WO | WO 99/03407 | A1 | 1/1999 |
| WO | WO 99/03408 | A1 | 1/1999 |
| WO | WO 99/03409 | A1 | 1/1999 |
| WO | WO 99/12483 | A1 | 3/1999 |
| WO | WO 99/12487 | A1 | 3/1999 |
| WO | WO 99/12488 | A1 | 3/1999 |
| WO | WO 99/15086 | A1 | 4/1999 |
| WO | WO 99/15091 | A1 | 4/1999 |
| WO | WO 99/23933 | A2 | 5/1999 |
| WO | WO 99/23959 | A1 | 5/1999 |
| WO | WO 99/25261 | A1 | 5/1999 |
| WO | WO 99/29244 | A1 | 6/1999 |
| WO | WO 99/34744 | A1 | 7/1999 |
| WO | WO 99/45849 | A1 | 9/1999 |
| WO | WO 99/48430 | A1 | 9/1999 |
| WO | WO 99/51158 | A1 | 10/1999 |
| WO | WO 00/24322 | A1 | 5/2000 |
| WO | WO 00/24330 | A1 | 5/2000 |
| WO | WO 00/41638 | A1 | 7/2000 |
| WO | WO 00/48506 | A1 | 8/2000 |
| WO | WO 00/53112 | A2 | 9/2000 |
| WO | WO 00/54653 | A1 | 9/2000 |
| WO | WO 00/57796 | A1 | 10/2000 |
| WO | WO 00/64365 | A1 | 11/2000 |
| WO | WO 00/72762 | A1 | 12/2000 |
| WO | WO 00/72765 | A1 | 12/2000 |
| WO | WO 01/03587 | A1 | 1/2001 |
| WO | WO 01/05702 | A1 | 1/2001 |
| WO | WO 01/10482 | A1 | 2/2001 |
| WO | WO 01/35845 | A1 | 5/2001 |
| WO | WO 01/54594 | A1 | 8/2001 |
| WO | WO 01/58371 | A1 | 8/2001 |
| WO | WO 01/62158 | A2 | 8/2001 |
| WO | WO 01/62161 | A1 | 8/2001 |
| WO | WO 01/62162 | A1 | 8/2001 |
| WO | WO 01/62164 | A2 | 8/2001 |
| WO | WO 01/62169 | A2 | 8/2001 |
| WO | WO 01/78605 | A2 | 10/2001 |
| WO | WO 01/91646 | A1 | 12/2001 |
| WO | WO 02/07608 | A2 | 1/2002 |
| WO | WO 02/07618 | A1 | 1/2002 |
| WO | WO 02/17799 | A1 | 3/2002 |
| WO | WO 02/19920 | A1 | 3/2002 |
| WO | WO 02/19932 | A1 | 3/2002 |
| WO | WO 02/30297 | A2 | 4/2002 |
| WO | WO 02/32322 | A2 | 4/2002 |
| WO | WO 02/36028 | A1 | 5/2002 |
| WO | WO 02/43571 | A2 | 6/2002 |
| WO | WO 02/058568 | A1 | 8/2002 |
| WO | WO 02/060328 | A1 | 8/2002 |

(56) References Cited

FOREIGN PATENT DOCUMENTS

| | | |
|---|---|---|
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

U.S. Appl. No. 12/031,573, filed Feb. 14, 2008.

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

International Search Report for PCT/US2010/059139, May 27, 2011 included in PCT Publication No. WO 2011/078959 A1 (39 pages).

\* cited by examiner

SURGICAL CUTTING INSTRUMENT THAT ANALYZES TISSUE THICKNESS

BACKGROUND

Surgical staplers are used to simultaneously make a longitudinal incision in tissue and apply lines of staples on opposing sides of the incision. Such instruments commonly include an end effector having a pair of cooperating jaw members that, if the instrument is intended for endoscopic or laparoscopic applications, are capable of passing through a cannula passageway. One of the jaw members receives a staple cartridge having at least two laterally spaced rows of staples—one on each side of the knife channel. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil. Simultaneously, a cutting instrument (or knife) is drawn distally along the jaw member so that the clamped tissue is cut and fastened (e.g., stapled) at the same time.

An example of a surgical stapler suitable for endoscopic applications is described in published U.S. patent application Pub. No. 2004/0232196 A1, entitled, "Surgical stapling instrument having separate distinct closing and firing systems," the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling actions avoid complications that may arise when performing such actions sequentially with different surgical tools that respectively only sever or staple.

Motor-driven endocutters are known in the art. In such devices, an electric motor powers the cutting and fastening action of the instrument. It is also known to use an on-board battery, located in the handle of the instrument, to power the motor. Published U.S. patent application Pub. No. 2007/0175952 A1, entitled "Motor-driven surgical cutting and fastening instrument with loading force feedback," the disclosure of which is herein incorporated by reference in its entirety, describes one such motor-driven surgical instrument.

SUMMARY

In one general aspect, the present invention is directed to a surgical instrument with a tissue-clamping end effector, where actuation of the instrument is locked out when the thickness of the tissue clamped in the end effector is not within a specified thickness range. According to various embodiments, the end effector comprises a tissue thickness module that senses the thickness of the tissue clamped in the end effector. The surgical instrument also comprises a control circuit in communication (e.g., wireless communication) with the tissue thickness module. The control circuit prevents actuation of a working portion of the end effector when the thickness of the tissue clamped in the end effector is not within the specified thickness range. In that way, actuation of the instrument can be locked out when too much or too little tissue is clamped in the end effector. This prevents the instrument from firing in situations where it should not be fired.

According to various implementations, the end effector comprises: first and second opposing jaw members; and a disposable cartridge (such as a disposable staple cartridge) located in the first jaw member. The tissue thickness module may be part of the disposable cartridge, and may comprise a Hall effect sensor. The second jaw member may comprise a magnet, where the Hall effect sensor senses a magnetic field strength from the magnet that is indicative of the thickness of the tissue clamped in the end effector. The tissue thickness module communicates data to the control circuit, the data comprising: (i) data indicative of the thickness of the tissue clamped in the end effector; and (ii) data indicative of a cartridge type of the disposable cartridge. The control circuit may comprise a processing unit programmed to determine whether the tissue clamped in the end effector is within the specified thickness range for the disposable cartridge based on the data communicated to the control circuit by the tissue thickness module. In that connection, the control circuit may comprise solid state memory that stores thickness range data for one or more cartridge types. The processing unit may be programmed to determine whether the tissue clamped in the end effector is within the specified thickness range for the disposable cartridge based on the data communicated to the control circuit by the tissue thickness module by comparing the data indicative of the thickness of the tissue clamped in the end effector to stored thickness range data for the cartridge type of the disposable cartridge in the end effector.

FIGURES

Various embodiments of the present invention are described herein by way of example in connection with the following figures, wherein.

DESCRIPTION

Certain embodiments of the present invention will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Such modifications and variations are intended to be included within the scope of the appended claims.

In general, embodiments of the present invention are directed to a surgical instrument that prevents firing of the instrument if the thickness of the tissue clamped in the end effector of the instrument is outside of acceptable limits (e.g., too thick or too thin). That way, the instrument can be prevented from firing in situations when it should not be fired. If the tissue thickness is not within the acceptable limits for the instrument, the operator (e.g., clinician) can adjust the tissue thickness or change the cartridge, for example.

Figure 1:
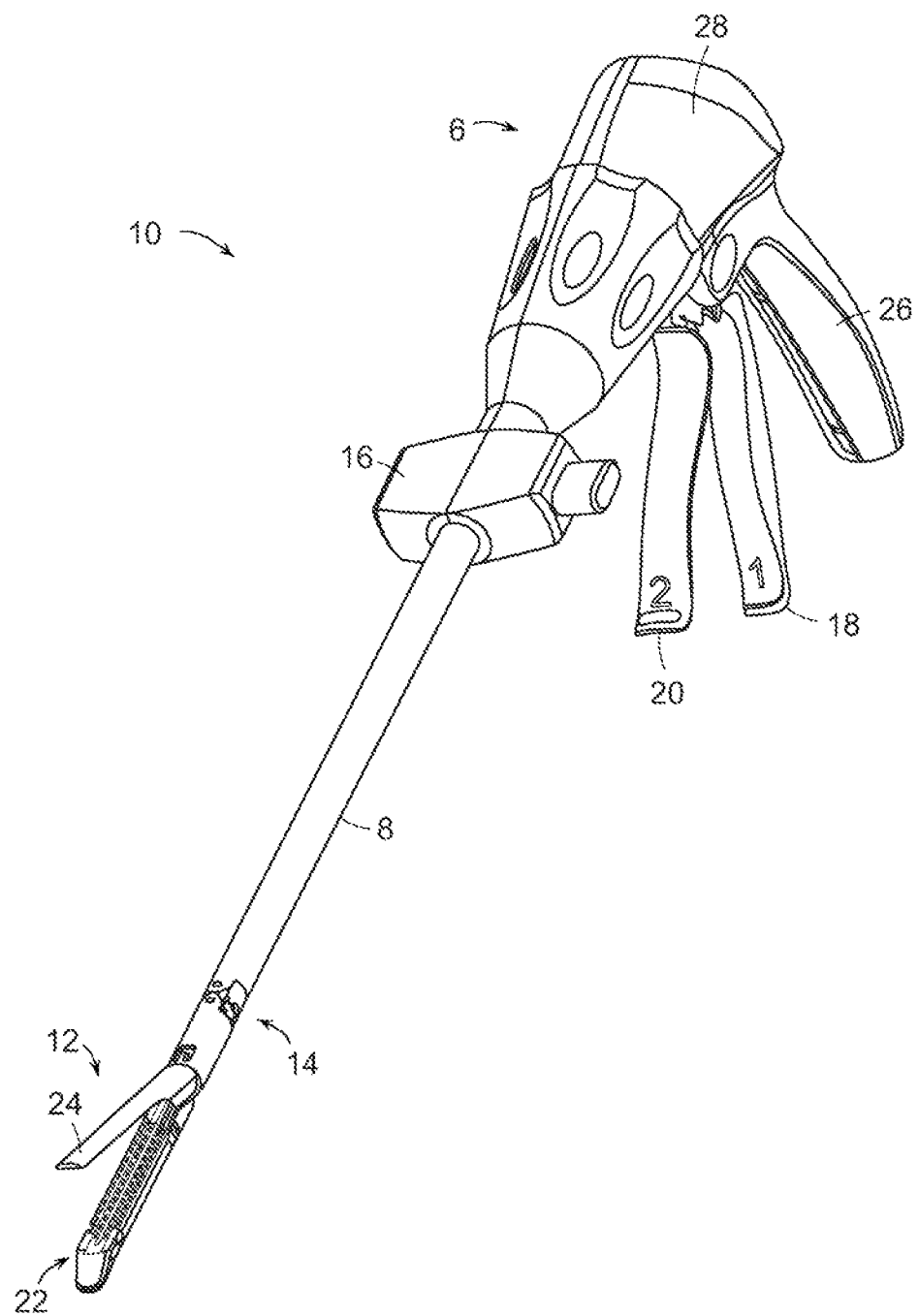
FIGS. 1-2 and 12 are views of a surgical instrument according to various embodiments of the present invention.
Figure 2:
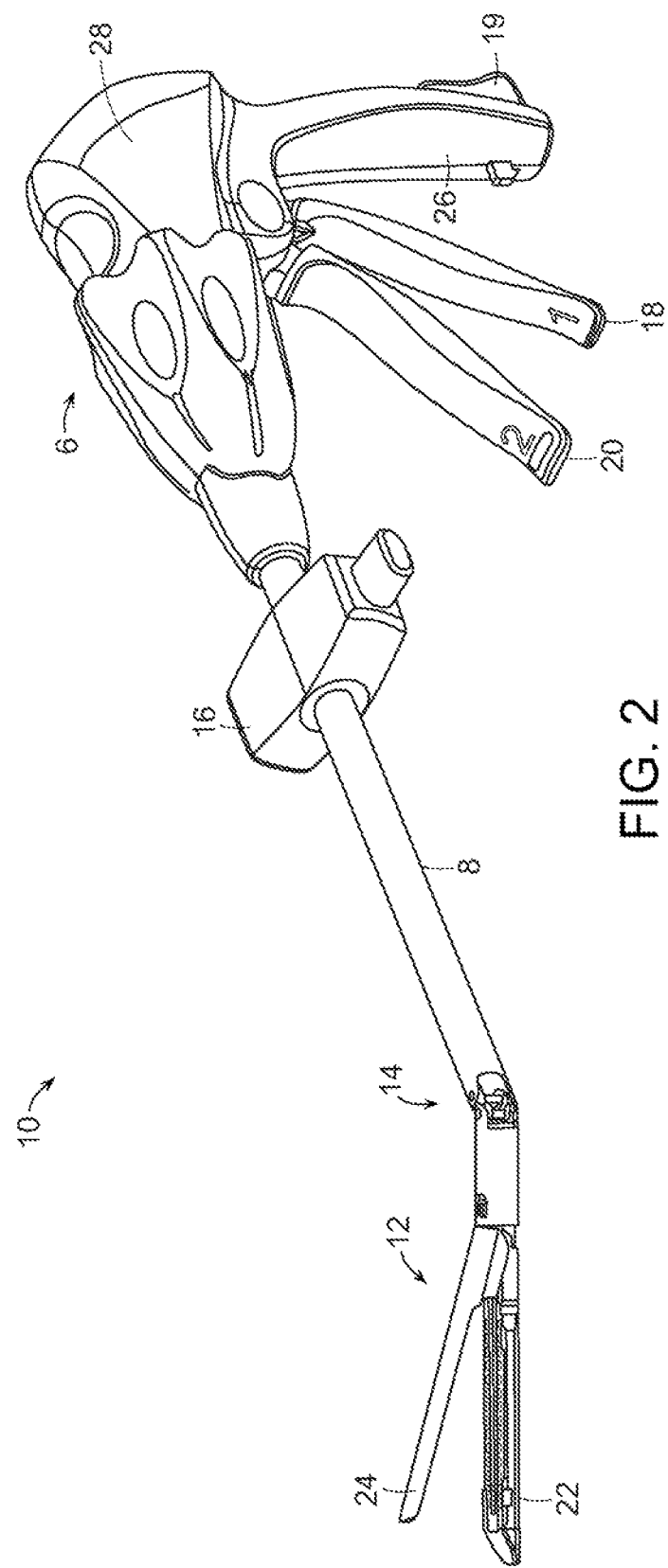

The instrument may be a motor-drive instrument or a hand-powered instrument, according to various embodiments. FIGS. 1 and 2 depict a motor-driven surgical cutting and fastening instrument 10 according to various embodiments of the present invention. The illustrated embodiment is a linear endoscopic instrument and, in general, the embodiments of the instrument 10 described herein are linear endoscopic surgical cutting and fastening instruments. It should be noted, however, that the invention is not so limited and that according to other embodiments of the present invention, the instrument may be another type of endoscopic instrument, such as a circular or curved endocutter. In addition, the instrument may be a non-endoscopic surgical cutting and fastening instrument, such as a laparoscopic or open instrument.

The surgical instrument 10 depicted in FIGS. 1 and 2 comprises a handle 6, a shaft 8, and an end effector 12 connected to the shaft 8. In various embodiments, the end effector 12 can be articulated about an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc. More details regarding RF devices may be found in U.S. Pat. No. 5,403,312 and U.S. patent application Ser. No. 12/031,573, entitled "Surgical cutting and fastening instrument having RF electrodes, filed Feb. 14, 2008, both of which are incorporated by reference in their entirety.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by the elongate shaft 8. In one embodiment, a clinician or operator of the instrument 10 may articulate the end effector 12 relative to the shaft 8 by utilizing the articulation control 16, as described in more detail in published U.S. patent application Pub. No. 2007/0158385 A1, entitled "Surgical Instrument Having An Articulating End Effector," by Geoffrey C. Hueil et al., which is incorporated herein by reference in its entirety.

The end effector 12 includes in this example, among other things, a staple channel 22 and a pivotally translatable clamping member, such as an anvil 24, which are maintained at a spacing that assures, when the anvil 24 is in its clamped position, effective stapling and severing of tissue clamped in the end effector 12. The handle 6 includes a downwardly extending pistol grip 26, towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position, the firing trigger 20 may rotate slightly toward the pistol grip 26 so that it can be reached by the operator using one hand. Then the operator may pivotally draw the firing trigger 20 toward the pistol grip 12 to cause the stapling and severing of clamped tissue in the end effector 12. In other embodiments, different types of clamping members besides the anvil 24 could be used. The handle 6 may also include an upper portion 28 that may sit on top of the user's hand when the user grips the pistol grip portion 26 with his/her hand.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

In operational use, the closure trigger 18 may be actuated first. Once the clinician is satisfied with the positioning of the end effector 12, the clinician may draw back the closure trigger 18 to its fully closed, locked position proximate to the pistol grip 26. Drawing back of the closure trigger 18 causes the anvil 24 to rotate downwardly, clamping the tissue between the anvil 24 and channel 27. The firing trigger 20 may then be actuated. Actuation of the firing trigger 20 causes the cutting instrument in the end effector 12 to sever the clamped tissue, and causes the fasteners in the end effector to fasten the severed tissue. The firing trigger 20 returns to the open position (shown in FIGS. 1 and 2) when the clinician removes pressure. A release button 19 on the handle 6, when depressed may release the locked closure trigger 18. The release button 19 may be implemented in various forms such as, for example, as disclosed in published U.S. patent application Pub. No. 2007/0175955, entitled "Surgical cutting and fastening instrument with closure trigger locking mechanism," which is incorporated herein by reference in its entirety.

The end effector 12 may include a cutting instrument, such as knife, for cutting tissue clamped in the end effector 12 when the firing trigger 20 is retracted by a user. The end effector 12 may also comprise means for fastening the tissue severed by the cutting instrument, such as staples, RF electrodes, adhesives, etc. More details regarding possible configurations of the end effector 12 may be found in the following patents and published patent applications, which are incorporated herein by reference in their entirety: U.S. Pat. Nos. 5,709,680; 5,688,270; 7,000,818; Pub. No. 2005/0173490 A1; Pub. No. 2006/0025809 A1; Pub. No. 2007/0102453 A1; No. 2007/0102452 A1; Pub. No. 2009/0206134 A1; and Pub. No. 2009/0206124 A1.

The instrument 10 may also comprise a closure system for closing (or clamping) the end effector upon closure (or retraction) of the closure trigger 18. More details regarding embodiments of an exemplary closure system for closing (or clamping) the anvil 24 of the end effector 12 by retracting the closure trigger 18 are provided in the following U.S. patent references, which are incorporated herein by reference in their entirety: Pub. No. 2004/0232196 A1, now U.S. Pat. No. 7,000,818; Pub. No. 2007/0175956 A1, now U.S. Pat. No. 7,644,848; Pub. No. 2007/0158385 A1, now U.S. Pat. No. 7,670,334; Pub. No. 2007/0175962 A1, now U.S. Pat. No. 7,442,139; U.S. Pat. No. 7,464,849; and the references cited in the paragraph above.

A longitudinally movable or rotatable drive shaft located within the shaft 8 of the instrument 10 may drive/actuate the cutting instrument and the fastening means in the end effector 12. An electric motor, located in the pistol grip portion 26 of the handle 6 of the instrument 10, may be used to drive, directly or indirectly (via a gear drive train), the drive shaft. In various embodiments, the motor may be a DC brushed driving motor having a maximum rotation of, approximately, 25,000 RPM. In other embodiments, the motor may include a brushless motor, a cordless motor, a synchronous motor, a stepper motor, or any other suitable electric motor. A battery (or "power source" or "power pack"), such as a Li ion battery, may be provided in the pistol grip portion 26 of the handle 6 adjacent to the motor. The battery supplies electric power to the motor via a motor control circuit. According to various embodiments, a number of battery cells connected in series may be used as the power source to power the motor. In addition, the power source may be replaceable and/or rechargeable.

As described in more detail below, operation of the motor may be controlled by a processor or microcontroller-based control circuit, which may be located in the handle 6 of the instrument 10, near the motor and battery pack. The control circuit may receive input from the end effector 12 relating to the thickness of the tissue clamped between the opposing jaws (e.g., the staple channel 22 and the anvil 24) of the end effector 12. The control circuit may be in communication with the tissue thickness sensing module of the end effector 12 wirelessly or via a wired connection. If the control circuit determines that the clamped tissue is not within acceptable limits (e.g., too thick or too thin) based on the input from the tissue thickness sensing module, the control circuit may lockout operation of the motor, thereby preventing operation of the instrument. Before describing the control circuit, a description of the end effector 12 and the tissue thickness sensing module is provided.

Figure 3:
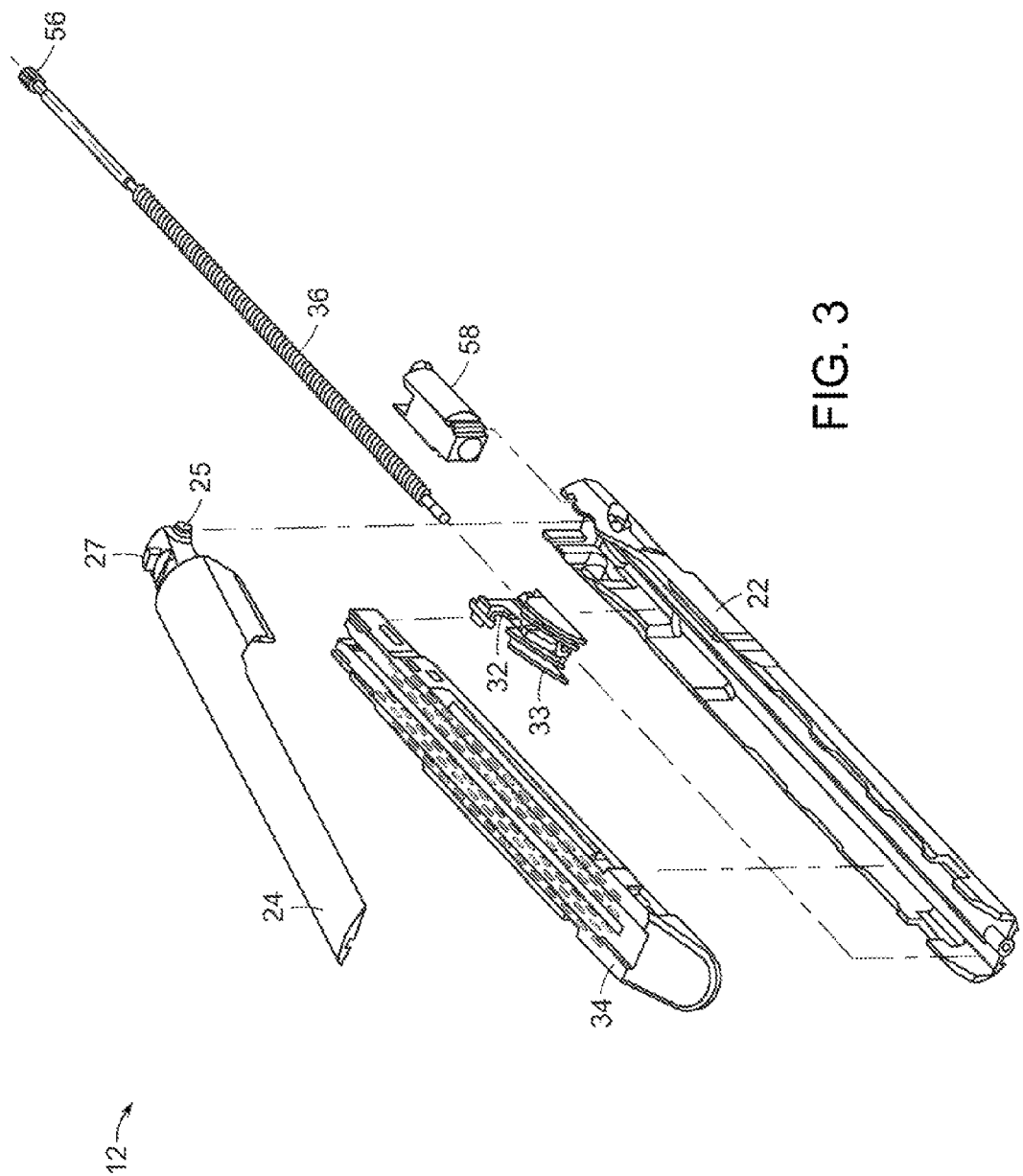
FIGS. 3-5 are exploded views of the end effector and shaft of a surgical instrument according to various embodiments of the present invention.

FIG. 3 is a diagram of the end effector 12 according to various embodiments of the present invention. As shown in the illustrated embodiment, the end effector 12 may include, in addition to the previously mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at pivot pins 25 connected to the proximate end of the channel 22. The anvil 24 may also include a tab 27 at its proximate end that is inserted into a component of the mechanical closure system to open and close the anvil 24. When the closure trigger 18 is actuated, that is, drawn in by a user of the instrument 10, the anvil 24 may pivot about the pivot pins 25 into the clamped or closed position, thereby clamping tissue between the channel 22 and the anvil 24. If clamping of the end effector 12 is satisfactory, the operator may actuate the firing trigger 20, which causes the knife 32 and sled 33 to travel longitudinally along the channel 22, thereby cutting the tissue clamped within the end effector 12. The movement of the sled 33 along the channel 22 causes the staples (not shown) of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled "SURGICAL STAPLING INSTRUMENT INCORPORATING AN E-BEAM FIRING MECHANISM" to Shelton, IV et al., which is incorporated herein by reference in its entirety, provides more details about such two-stroke cutting and fastening instruments. The sled 33 may be part of the cartridge 34, such that when the knife 32 retracts following the cutting operation, the sled 33 does not retract.

Figure 4:
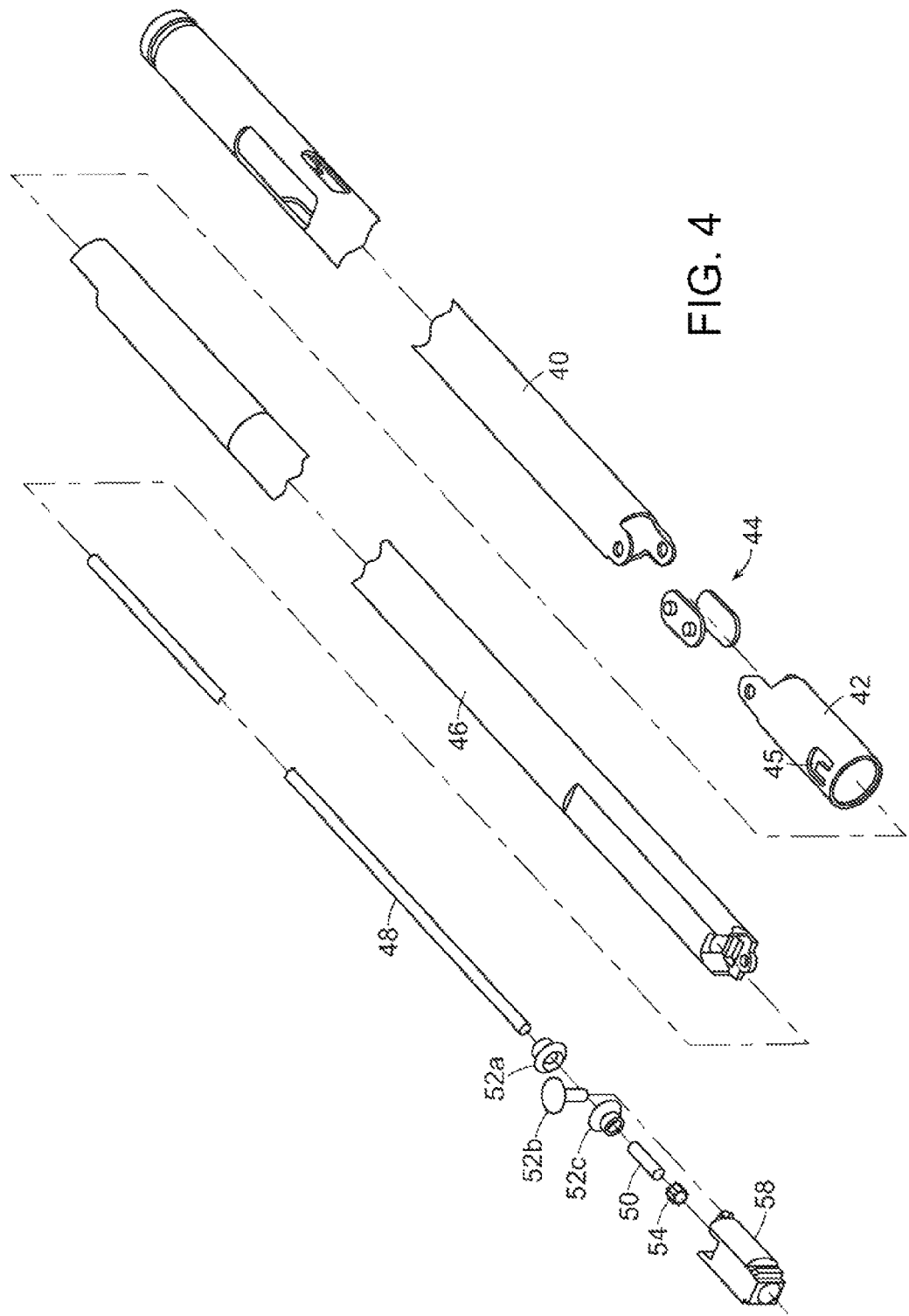
Figure 5:
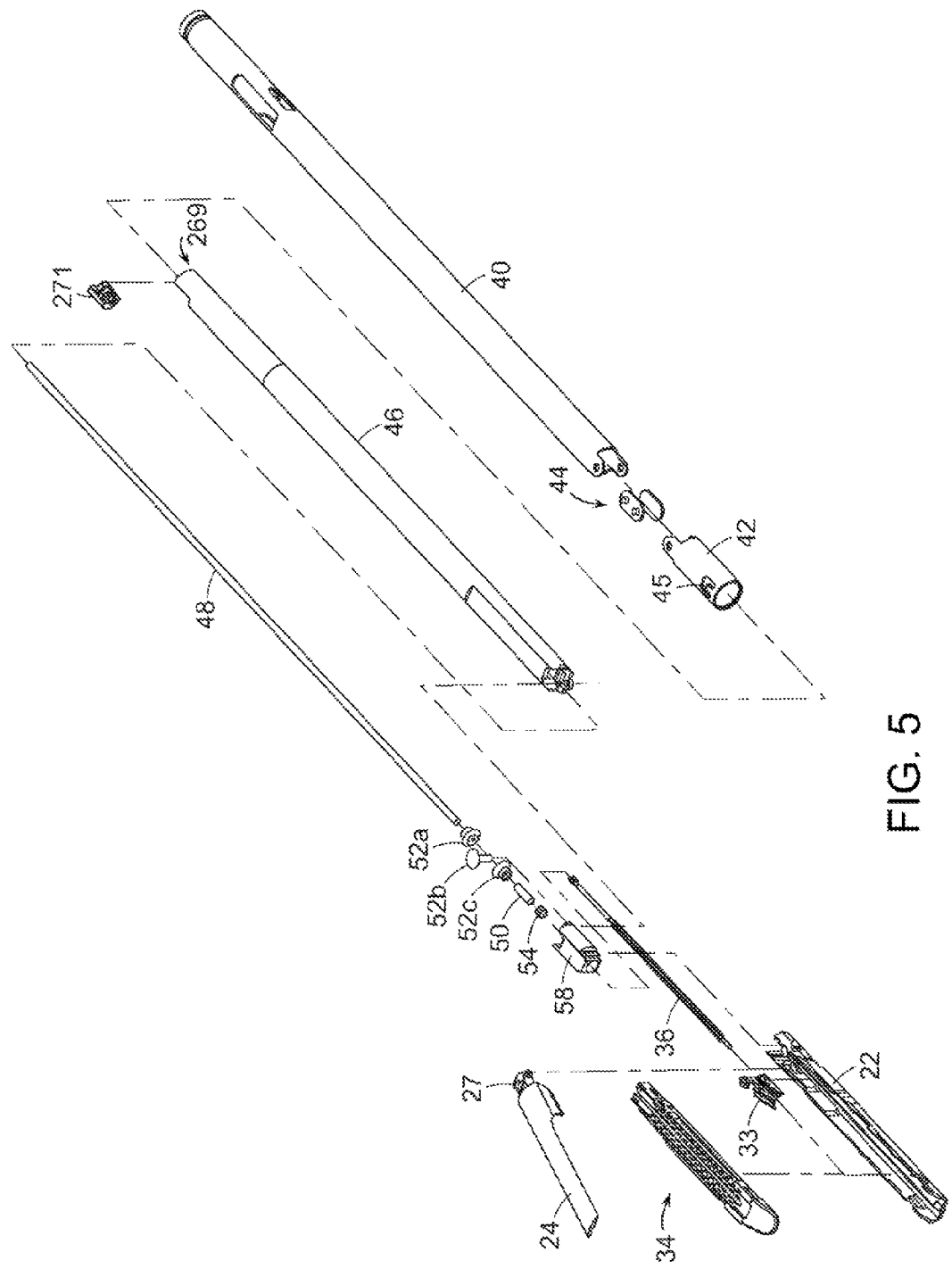
Figure 6:
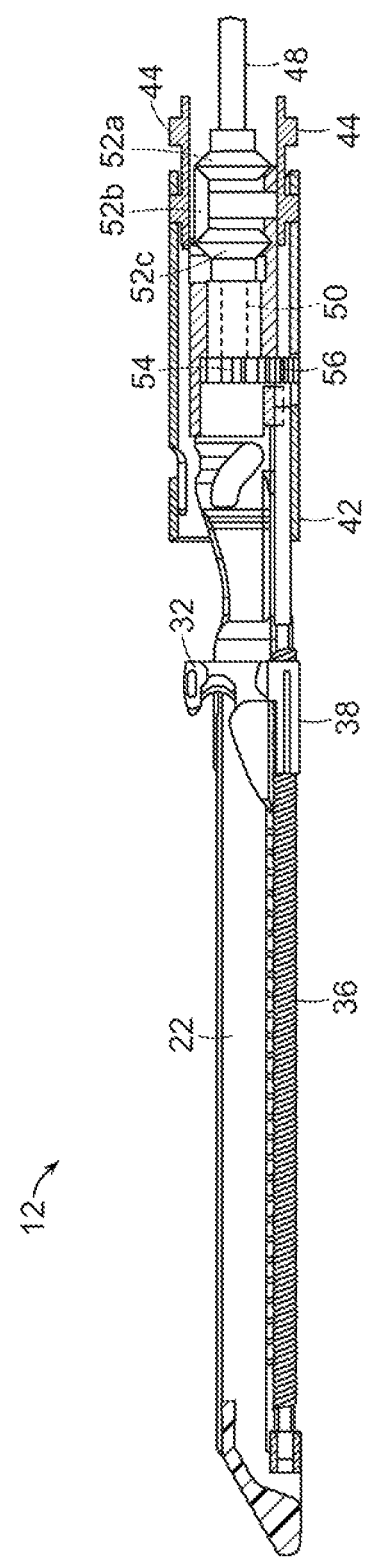
FIGS. 6-7 are views of the end effector according to various embodiments of the present invention.

FIGS. 4-5 are exploded views and FIG. 6 is a side view of the end effector 12 and shaft 8 according to various, non-limiting embodiments. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40,42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52 *b* may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52 *a-c*) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20, the bevel gear assembly 52 *a-c* causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

In the illustrated embodiment, the end effector uses a rotatable, helical screw shaft 36 to drive the cutting instrument 32. Such a helical drive screw may be used in embodiments where a rotating drive member is used. In other embodiments, a longitudinally reciprocating drive member may be used to power the cutting instrument. The end effector 12 may be modified accordingly to suit such a longitudinally reciprocating drive member. More details regarding such end effectors may be found in U.S. Pat. Nos. 7,140,528 and 7,000,819, which are incorporated herein by reference in their entirety.

Figure 7:
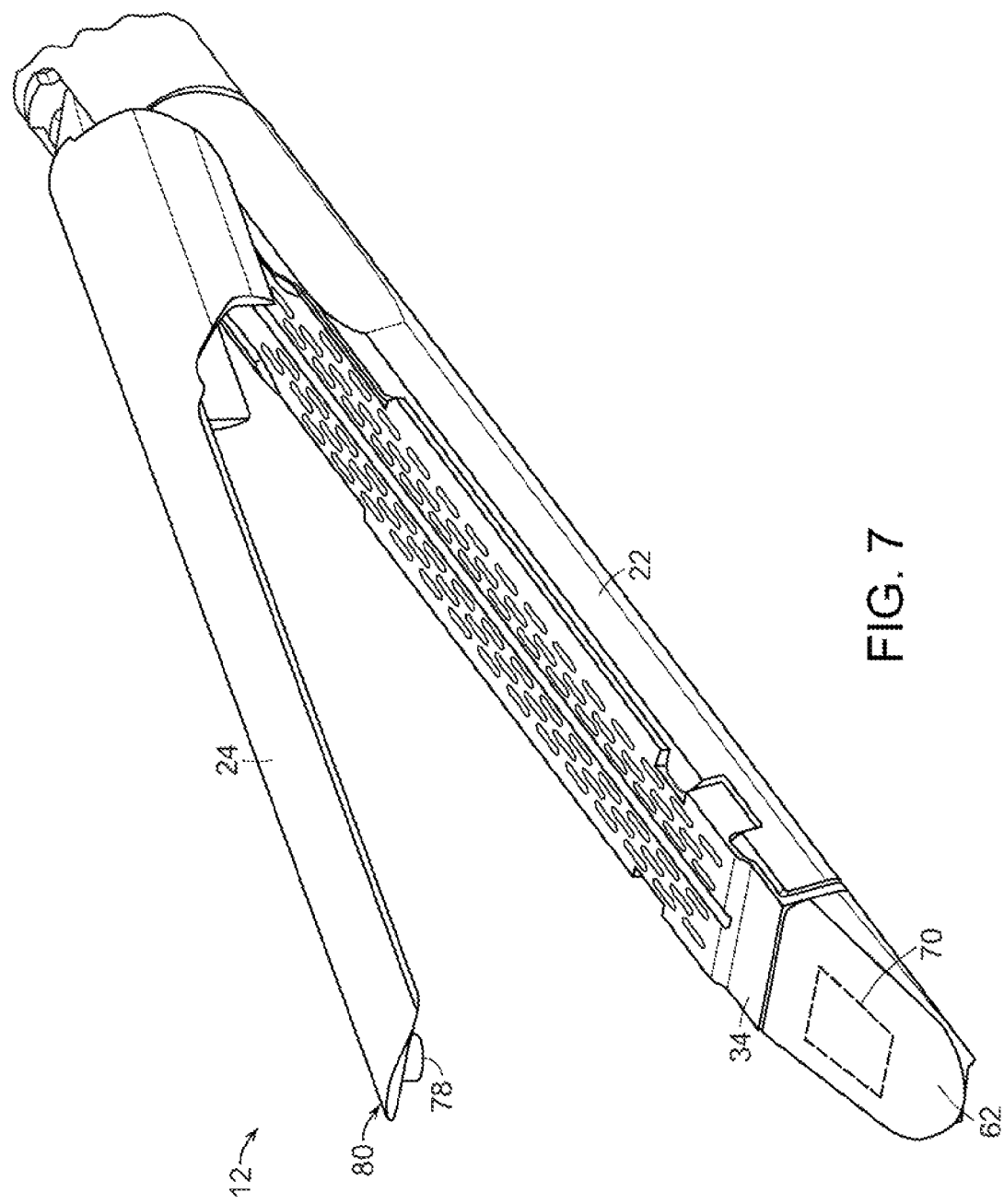
Figure 8:
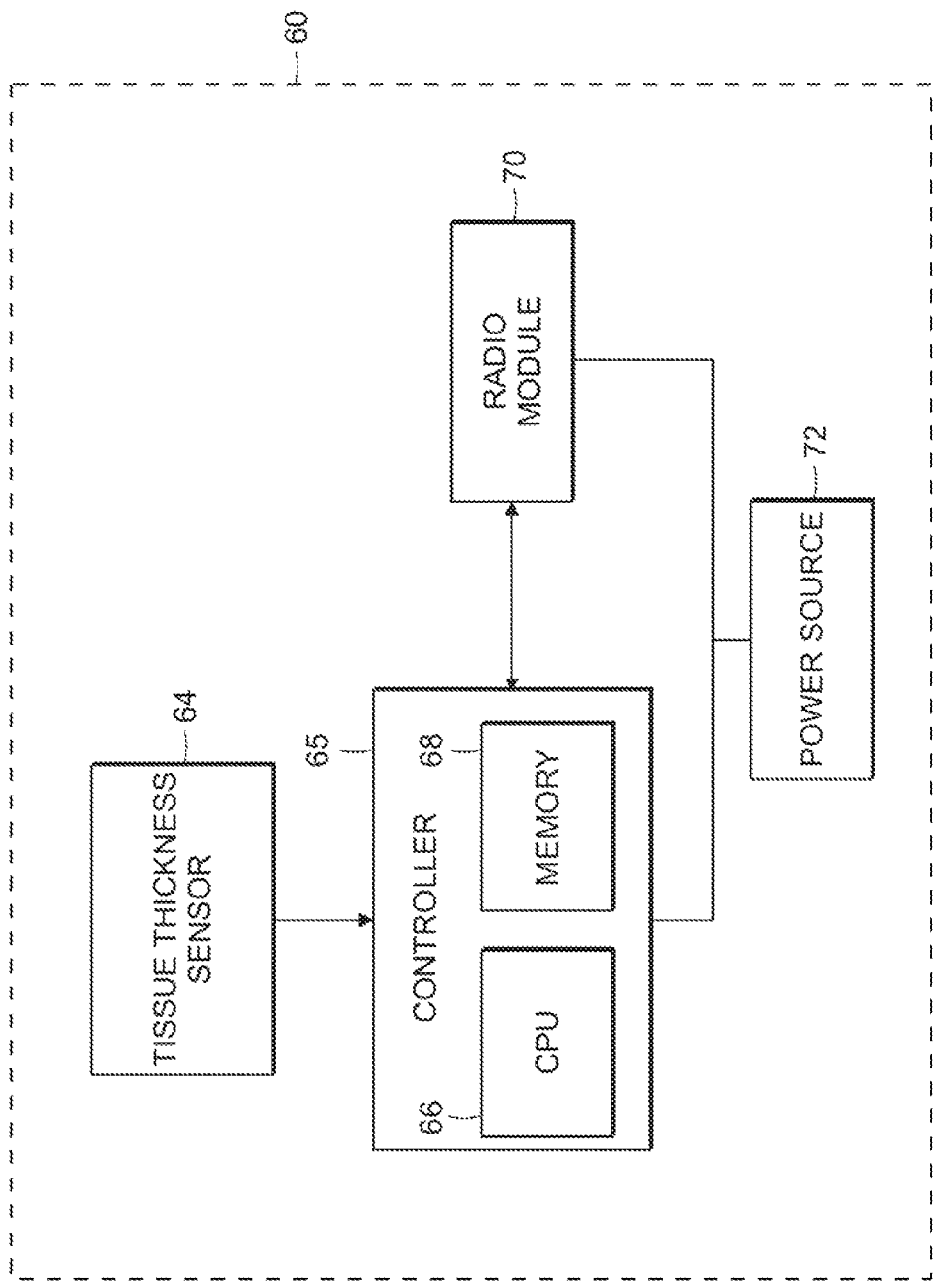
FIG. 8 is a block diagram of a tissue thickness module according to various embodiments of the present invention.

According to various embodiments, the replaceable staple cartridge 34 may comprise a tissue thickness sensing module that senses the thickness of tissue clamped in the end effector 12 between the staple channel 22 (including the staple cartridge 34) and the anvil 24. According to various, non-limiting embodiments, as shown in FIG. 7, the tissue thickness sensing module 60 may be located at a distal end 62 of the staple cartridge 34, such that it is out of the way of the staples of the staple cartridge 34 when the staples are fired. FIG. 8 is a block diagram of the tissue thickness sensing module 60 according to various embodiments. As shown in FIG. 8, the tissue thickness sensing module 60 may comprise a tissue thickness sensor 64, a controller 65, a radio module 70, and a power source 74. The controller 65 may comprise a processor unit (CPU) 66 and a memory unit 68. In various embodiments, the tissue thickness sensor 64 may comprise a Hall effect sensor that detects the thickness of the tissue clamped in the end effector 12 based on the magnetic field from a magnet 78 located, for example, at a distal end 80 of the anvil 24, as shown in FIG. 7. When the clinician closes the anvil 24 by retracting the closure trigger 18, the magnet 78 rotates downwardly closer to the sensor 64, thereby varying the magnetic field detected by the sensor 64 as the anvil 24 rotates into the closed (or clamped position). The strength of the magnetic field from the magnet 78 and sensed by the sensor 64 is indicative of the distance between the channel 22 and the anvil 24, which is indicative of the thickness of the tissue clamped between the channel 22 and the anvil 24 when the end effector 12 is in the closed (or clamped) position.

The memory unit 68 of the controller 65 may comprise one or more solid state read only memory (ROM) and/or random access memory (RAM) units. In various embodiments, the CPU 66 and the memory unit(s) 68 may be integrated into a single integrated circuit (IC), or multiple ICs. The ROM memory unit(s) may comprise flash memory. The ROM memory unit(s) may store code instructions to be executed by the CPU 66 of the controller 65. In addition, the ROM memory unit(s) may store data indicative of the cartridge type of the cartridge 34. That is, for example, ROM memory unit(s) 68 may store data indicating the model type of staple cartridge 34. As explained further below, the motor control circuit in the handle 6 of the instrument 10 may utilize the tissue thickness information and the model type of the staple cartridge 34 to determine if the tissue clamped in the end effector 12 is too thick or too thin, based on the specified tissue thickness range for the particular staple cartridge 34. The radio module 70 may be a low-power, 2-way radio module that communicates wirelessly, using a wireless data communication protocol, with the motor control circuit in the handle 6 of the instrument 10. According to various embodiments, the radio module 70 may communicate with the motor control circuit using a communication frequency that is suitable for transmission through human tissue. The communications between the radio module 70 and the motor control circuit may use the MICS (Medial Implant Communication Service) frequency band (402-405 MHz), a suitable industrial, scientific and medical (ISM) radio band (such as 433 MHz center frequency or 915 MHz center frequency), or any other suitable, human-tissue-permeable frequency band. The power source 74 may comprise a suitable battery cell for powering the components of the tissue thickness sensing module 60, such as a Lithium-ion battery or some other suitable battery cell.

Figure 9:
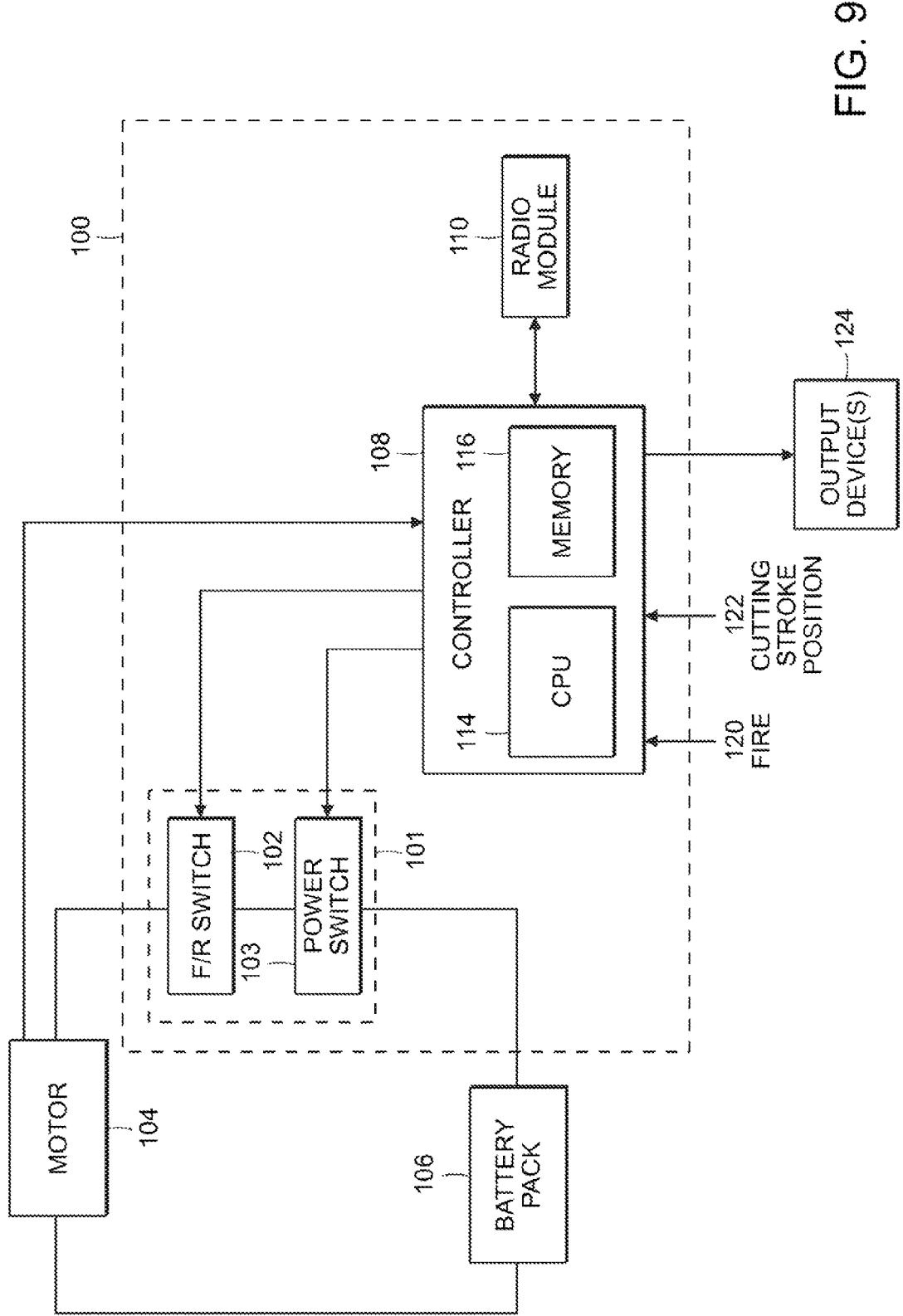
FIG. 9 is a block diagram of a motor control circuit according to various embodiments of the present invention.

FIG. 9 is a diagram of the motor control circuit 100 according to various, non-limiting embodiments. The motor control circuit 100 may be located in the handle 6 of the instrument 10, in close proximity with the motor 104 and battery pack 106, and spaced away from the tissue thickness sensing module 60 in the end effector 12 by the shaft 8, for example. As such, the motor control circuit 100 may wirelessly communicate with the tissue thickness sensing module 60 as described herein, although in other embodiments, there may be a wired connection, with wires running through the shaft 8 between the motor control circuit 100 and the tissue thickness sensing module 60 to handle the communications therebetween.

Figure 10:
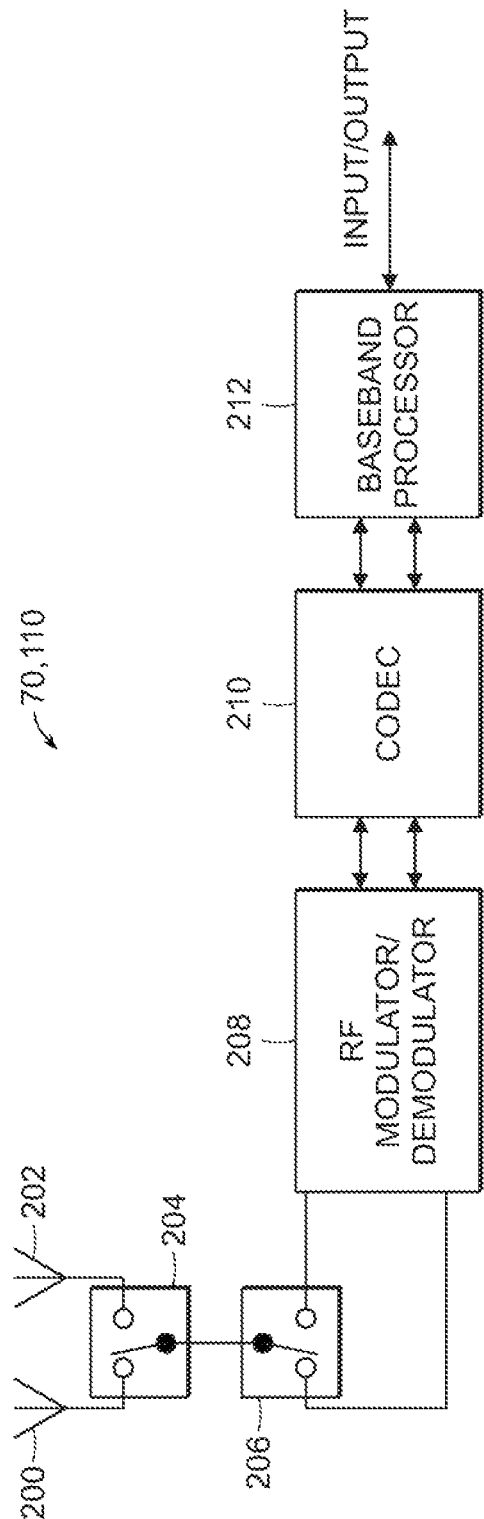
FIG. 10 is a block diagram of a radio module according to various embodiments of the present invention.

As shown in FIG. 9, the motor control circuit 100 may comprise, according to various embodiments, a power switching circuit 101, a controller 108, and a radio module 110. The radio module 110 may communicate with the radio module 70 of the tissue thickness sensing module 60. Therefore, the radio module 100 may be a low, power module that operates at the same frequency as the radio module 70 and uses the same communication protocol. The radio modules 70, 100, as shown in FIG. 10, may both comprise, according to various embodiments, transmit and receive antennas 200, 202, an antenna switch 204, a transmit/receive switch 206, RF modulator/demodulator 208, a coder/decoder (codec) 210, and a baseband processor 212. The antennas 200, 2002 of the motor control circuit 100 and the tissue thickness sensing module 60 may be microstrip antennas, for example.

The power switching circuit 101 may comprise, according to various embodiments, a power switch 103 and a forward/reverse switch 102, that collectively connect the motor 104 and the battery pack 106 in order to connect power from the battery pack 106 to the motor 104. In various embodiments, the forward/reverse switch 102 may comprise a double-pole/double throw relay that, depending on its polarity, determines whether the motor 104 forward rotates or reverse rotates. The controller 108 may control the operation of the switches 102-103. In various embodiments, the controller 108 may be implemented as a microcontroller that comprises a processing unit (CPU) 114 and memory 116. The memory 116 may comprise solid state ROM and/or RAM memory units. The ROM memory unit(s) may comprise instruction code that is executed by the processing unit 114. The processing unit 114 and the memory 116 may be integrated into a single IC, or multiple ICs may be used. The controller 108 and radio module 112 of the motor control circuit 100 may be powered by the battery pack 106.

As shown in FIG. 9, the controller 108 may receive a number of inputs and, based on processing of those inputs, may control the switches 102-103, to thereby appropriately control the motor 104 of the instrument 10. The inputs to the controller 108 may include a fire input 120, a cutting instrument position input 122, and any other suitable inputs. The fire input 120 may indicate the status of the firing trigger 20, such as whether the clinician has retracted the firing trigger 20 to commence a cutting stroke by the knife in the end effector 12 and whether the clinician has let go of the firing trigger 20 to end the cutting stroke. The fire input 120 may be from a sensor, such as a proportional switch, responsive to the firing trigger 20. The cutting instrument position input 122 may indicate the position of the cutting instrument 34 in the end effector 12 in the course of the cutting stroke. The controller 108 may use this input to determine the position of cutting instrument 34 in the cutting stroke, such as whether the cutting instrument 34 is near or at the end of the cutting stroke. As the cutting instrument 34 approaches the end of the cutting stroke, the controller 108 may reduce the rotation rate of the motor 104, and may reverse the rotation of the motor 104 when the cutting instrument 34 reaches the end of the cutting stroke. The controller 108 may also reduce the rate of rotation of the motor 104 when the cutting instrument is close to its initial, home position at the proximate end of the end effector 12 when the cutting instrument is retracted, and may stop the motor 104 when the cutting instrument is fully retracted. More details regarding a proportional firing trigger switch are provided in the following U.S. patent references, which are incorporated herein by reference in their entirety: Pub. No. 2007/0175957; Pub. No. 2007/0175958; and Pub. No. 2007/0175959. More details regarding instruments with cutting instrument position sensors are provided in the following U.S. patent references, which are incorporated herein by reference in their entirety: application Ser. No. 12/235,782; and application Ser. No. 12/235,972.

Of course, the controller 108 also receives input data from the tissue thickness sensing module 60 via the radio module 110. The input data from the tissue thickness sensing module 60 may include: (i) the tissue thickness data as sensed by the sensor 64 of the tissue thickness sensing module 60; and (ii) the cartridge model data indicative of the model type of the staple cartridge 34, which is stored in the memory 68 of the tissue thickness sensing module 60. Based on this data, the controller 108 of the motor control circuit 100 may determine whether the tissue clamped in the end effector 12 is within the specified range for the specific staple cartridge 34. If the tissue thickness is within the specified range, the controller 108 may control the switches 102-103 such that power is connected to the motor 104 (assuming other input data is appropriate). On the other hand, if the tissue thickness is not within the specified range, the controller 108 may control the switch 103 such that power is not connected to the motor 104, thereby locking out the motor 104 based on the tissue thickness and preventing operation of the instrument 10.

Figure 11:
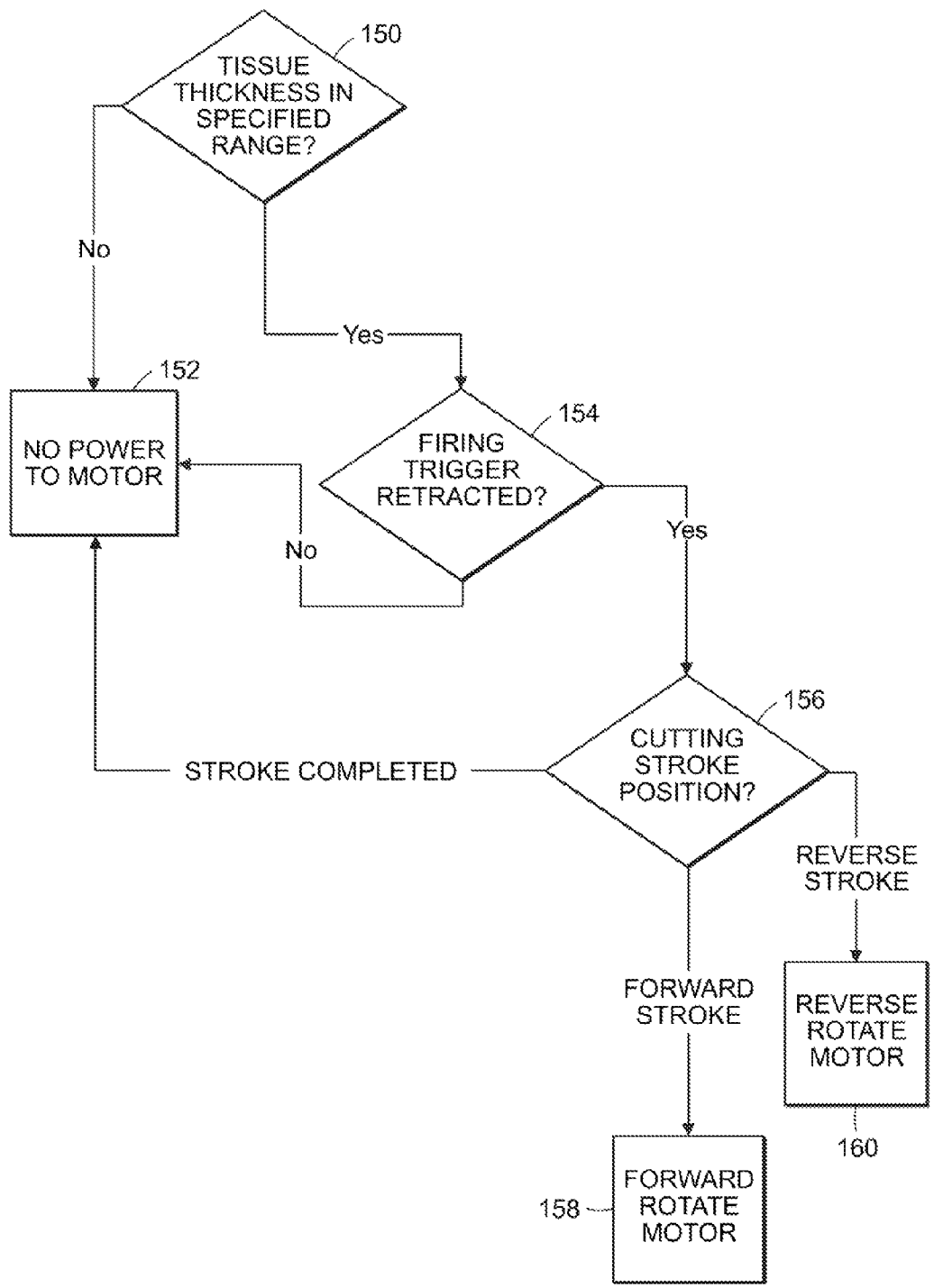
FIG. 11 is flow chart of a process executed by the motor control circuit according to various embodiments of the present invention.

FIG. 11 is a flowchart of a process executed by the controller 108 according to various embodiments. The process may be executed by the processing unit 114 by executing code stored in the memory 116. The process may start at step 150, where the controller 108 determines whether the thickness of the tissue clamped in the end effector 12 is within the specified range for the particular staple cartridge 34. The controller 108 may determine this by comparing the tissue thickness data from the sensor 64 to the specified range for the particular staple cartridge 34. The controller 108 may determine the specified thickness range for the staple cartridge using (i) the staple cartridge model data transmitted from the tissue thickness sensing module 60 and (ii) a look-up table (or other data storage structure) in the memory 116 of the controller, which table stores data indicating the specified thickness range for a number of staple cartridge model types. The specified thickness range may include a minimum thickness and a maximum thickness for each model type. For example, different cartridge model types may have different length staples. Longer staples may be able to accommodate more tissue in the end effector than cartridges with shorter staple lengths. As such, the upper thickness limit may be greater for cartridges with longer staples, and the lower thickness limit may be lower for cartridges with shorter staple lengths. If the clamped tissue thickness is less than the minimum thickness or greater than the maximum thickness for the model type of the cartridge 34, the tissue thickness is outside of the specified range.

If the tissue thickness is outside of the specified thickness range for the staple cartridge 34, the process advances to step 152, where the controller 108 controls the power switch 103 such that power switch 103 is in an open, non-conducting state, so that power from the battery pack 106 is not coupled to the motor 104. As such, the motor 104 does not receive power and is locked out of operation, thereby preventing actuation of the end effector 12. On the other hand, if the tissue thickness is within the specified thickness range for the staple cartridge 34, the process advances to step 154, where the controller 108 determines whether the firing trigger 20 is retracted based on the fire input 120. If it is not, the process advances to step 152 so that power from the battery pack 106 is not coupled to the motor 104. If, on the other hand, the firing trigger 20 is retracted, the process advances to step 156, where the controller 108 determines the position of the cutting instrument 34 in the cutting stroke based on the cutting instrument position input 22. If the position of the cutting instrument is in the forward stroke, the process advances to step 158, where the controller 108 outputs a control signal to the forward/reverse switch 102 to cause the forward/reverse switch 102 to be in a state that couples power to the motor 104 such that the motor 104 forward rotates. Conversely, if the position of the cutting instrument in the cutting stroke requires reverse rotation of the motor 104, the process advances to step 160, where the controller 108 outputs a control signal to the forward/reverse switch 102 to cause the forward/reverse switch 102 to be in a state that couples power to the motor 104 such that the motor 104 reverse rotates. The process may run in an ongoing manner throughout a surgical procedure involving the instrument 10. That way, if for some reason the tissue thickness goes out of range during the procedure, the controller 108 can take appropriate action in response to the real-time tissue thickness data received from the tissue thickness module 60.

Returning to FIG. 9, the controller 108 may also receive feedback from the motor 104 regarding conditions of the motor 104, such as rate of rotation, rotation direction, etc. The controller 108 may use the data in controlling the motor 104. Also, the controller 108 may output control signals to one or more output devices 124. The output devices 124 may comprise visual indicators, such as illuminators (e.g., light emitting diodes), and/or audible indicators, such as speakers. For example, the output devices 124 may comprise a number of LEDs located on the outside of the handle 6 of the instrument and visible to the operator of the instrument 10 when the instrument 10 is in use. One LED may be turned on when the clamped tissue thickness is in the specified thickness range for the staple cartridge; a second LED may be turned on when the clamped tissue thickness is outside the specified thickness range for the staple cartridge; a third LED may be turned on when the motor 104 is forward rotating; a fourth LED may be turned on when the motor 104 is reverse rotating; etc.

Figure 12:
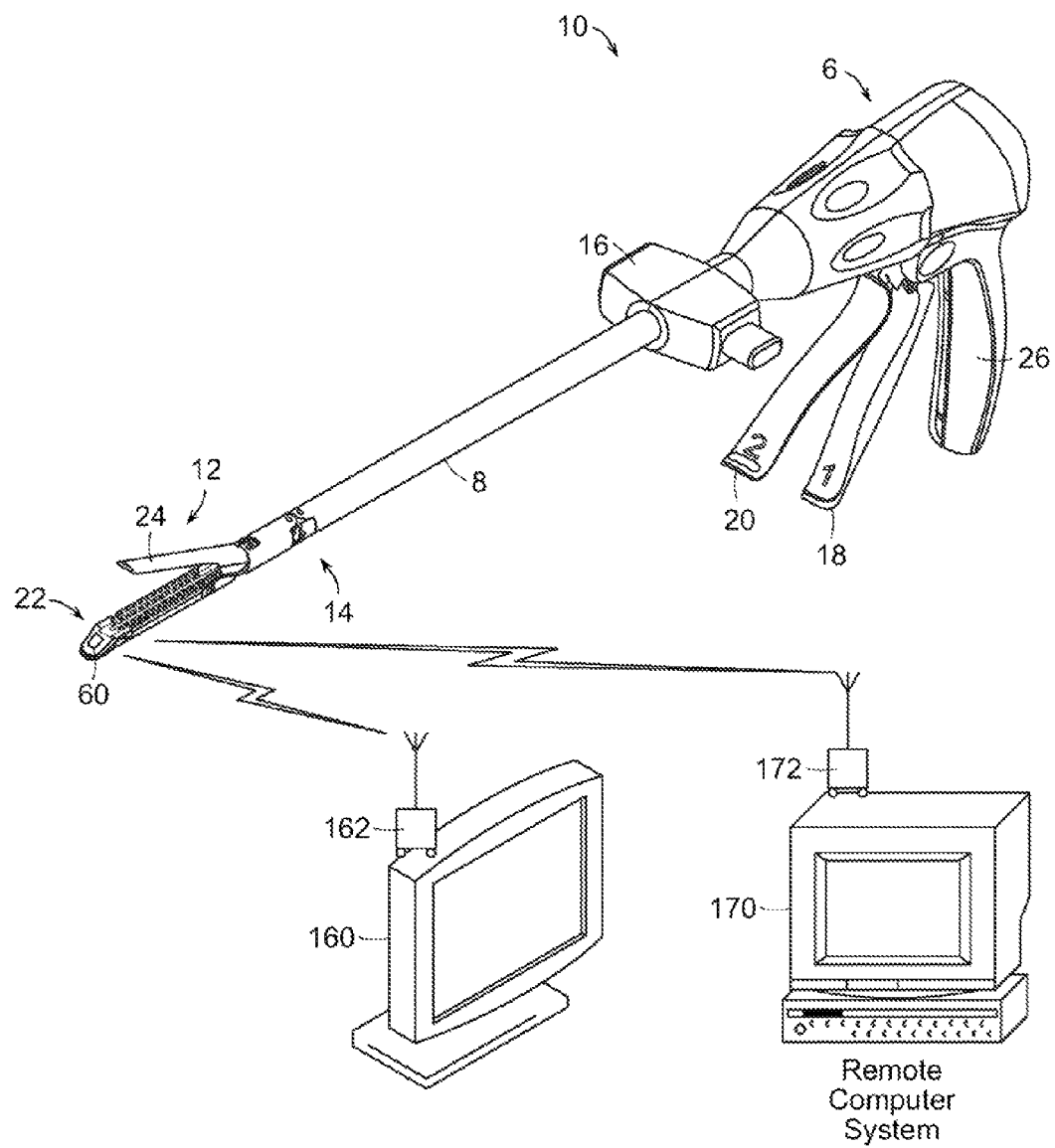

In addition, in other embodiments, the transmissions from the tissue thickness module 60 may be received by a receiver other than the motor control circuit 100. For example, with reference to FIG. 12, the transmissions from the tissue thickness module 60 may be received by a visual display unit 160 and/or a computer system 170. The visual display unit 160 may comprise a RF radio module 162 for communicating with the tissue thickness module 60. Images based on data from the tissue thickness module 60 may be displayed on the display 160. That way, the clinician may see real-time data regarding the thickness of the clamped tissue throughout a procedure involving the instrument 10. The visual display unit 160 may comprise a monitor, such as a CRT monitor, a plasma monitor, a LCD monitor, or any other suitable visual display monitor. Similarly, the computer system 170 may comprise a RF radio module 172 for communicating with the tissue thickness module 60. The computer system 170 may store the data from the tissue thickness module 60 in a memory unit (e.g., a ROM or hard disk drive) and may process the data with a processor.

The surgical instruments disclosed herein can be designed to be disposed of after a single use, or they can be designed to be used multiple times. In either case, however, the device can be reconditioned for reuse after at least one use. Reconditioning can include any combination of the steps of disassembly of the surgical instrument, followed by cleaning or replacement of particular pieces, and subsequent reassembly. In particular, the surgical instrument can be disassembled, and any number of the particular pieces or parts of the device can be selectively replaced or removed in any combination. Upon cleaning and/or replacement of particular parts, the surgical instrument can be reassembled for subsequent use either at a reconditioning facility, or by a surgical team immediately prior to a surgical procedure. Those skilled in the art will appreciate that reconditioning of a surgical instrument can utilize a variety of techniques for disassembly, cleaning/replacement, and reassembly. Use of such techniques, and the resulting reconditioned surgical instrument, are all within the scope of the present application.

Preferably, the surgical instrument described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

In various embodiments, some components of the instrument 10 may be part of a removable, replaceable pack that may be inserted into the instrument 10 after the instrument 10 has been sterilized. For example, with reference to FIG. 9, in various embodiments, the battery pack 106, the controller 108, and the radio module 110 may be part of a removable, replaceable pack 140 that may be inserted into the handle 6 of the instrument 10 after the instrument has been sterilized. For example, the removable, replaceable pack 140 may be transferred aseptically to the instrument 10 after the instrument has been sterilized. In such an embodiment, the pack 140 may have appropriate external connectors for connecting to the motor 104, the switching circuit 101, the inputs 120, 122, and output devices 124, etc. In such an embodiment, therefore, the pack 140 can be reused in multiple instruments 10. The cartridge 34 may be disposed of after each use.

The above embodiments were described in the context of linear endocutter devices with a staple cartridge. It should be noted that the tissue thickness module 60 and corresponding control circuit 100 may be used in any surgical instrument having an end effector used to clamp tissue where thickness of the clamped tissue is an important consideration in the procedure. For example, the tissue thickness module 60 and corresponding control circuit 100 may be used in circular endocutters or other types of cutting/fastening devices, such as laproscopic devices. Also, the tissue thickness module 60 and corresponding control circuit 100 does not need to be used in a device using staples to fasten the severed tissue, but could also be used in instruments using other means to fasten the severed tissue, as noted above. Also, the tissue thickness module 60 and corresponding control circuit 100 do not need to be used in instruments having a motor. In such embodiments, the instrument 10 may employ a mechanical lockout to prevent firing. One such lockout mechanism is described in published U.S. application Pub. No. 2006/0025811, which is incorporated herein by reference in its entirety.

In various embodiments, therefore, the present invention is directed to a surgical instrument 10 that comprises a tissue-clamping end effector 12. In various embodiments, the end effector 12 comprises a moveable working instrument (e.g., a cutting instrument) 34 and a tissue thickness module 60 that senses the thickness of tissue clamped in the end effector 12. The surgical instrument 10 also comprises a control circuit 100 in communication with the tissue thickness module, where the control circuit prevents actuation of the working instrument when the thickness of the tissue clamped in the end effector is not within a specified thickness range. According to various implementations, the end effector comprises: first and second opposing jaw members 22, 24; and a disposable cartridge 34 (such as a disposable staple cartridge) located in the first jaw member 22, where the tissue thickness module is part of the disposable cartridge. Also, the tissue thickness module may comprise a Hall effect sensor 64, and the second jaw member comprises a magnet 78, where the Hall effect sensor senses a magnetic field strength from the magnet that is indicative of the thickness of the tissue clamped in the end effector when the end effector is in the closed (or clamped) position. In addition, the tissue thickness module communicates data to the control circuit, the data comprising: (i) data indicative of the thickness of the tissue clamped in the end effector; and (ii) data indicative of a cartridge type of the disposable cartridge.

The control circuit may comprise a processing unit 114 programmed to determine whether the tissue clamped in the end effector is within the specified thickness range for the disposable cartridge based on the data communicated to the control circuit by the tissue thickness module, including the data indicative of the thickness of the tissue clamped in the end effector and the data indicative of the cartridge type of the disposable cartridge. Additionally, the control circuit may comprise solid state memory 116 that stores thickness range data for one or more cartridge types. The processing unit may be programmed to determine whether the tissue clamped in the end effector is within the specified thickness range for the disposable cartridge based on the data communicated to the control circuit by the tissue thickness module by comparing the data indicative of the thickness of the tissue clamped in the end effector to stored thickness range data for the cartridge type of the disposable cartridge in the end effector.

In addition, the surgical instrument may further comprises an electric motor 104 that actuates the drive shaft 48, 50, and a battery pack 106 that supplies electrical power to the electric motor. The control circuit may prevent actuation of the electric motor when the thickness of the tissue clamped in the end effector is not within a specified thickness range.

Also, in various embodiments, the tissue thickness module is in wireless communication with the control circuit. The tissue thickness module may comprise a first radio module and the control circuit may comprise a second radio module, where the first radio module wirelessly communicates with the second radio module. In addition, the tissue thickness module may be in communication with a remote visual display unit or a remote computer system.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument comprising:
   an electric motor;
   a power source connected to the electric motor via at least one switch, wherein the power source is for supplying electric power to the electric motor;
   a tissue-clamping end effector that comprises:
      a moveable working portion that is moveable upon actuation of the electric motor;
      a removable cartridge that comprises a tissue thickness module that senses thickness of tissue clamped in the end effector; and
   a control circuit in communication with the tissue thickness module, wherein the control circuit automatically prevents actuation of the moveable working portion when the thickness of the tissue clamped in the end effector is not within a specified thickness range by controlling the at least one switch that connects the power source to the electric motor based on at least:
thickness data from the tissue thickness module for the tissue clamped in the end effector; and
model type data for the removable cartridge from the tissue thickness module.

2. The surgical instrument of claim 1, wherein the end effector comprises:
first and second opposing jaw members; and
wherein the removable cartridge is located in the first jaw member, and wherein the tissue thickness module is part of the removable cartridge.

3. The surgical instrument of claim 2, wherein:
the tissue thickness module comprises a Hall effect sensor; and
the second jaw member comprises a magnet, wherein the Hall effect sensor senses a magnetic field strength from the magnet that is indicative of the thickness of the tissue clamped in the end effector.

4. The surgical instrument of claim 3, wherein the tissue thickness module communicates to the control circuit:
the thickness data from the tissue thickness module for the tissue clamped in the end effector; and
the model type data for the removable cartridge from the tissue thickness module.

5. The surgical instrument of claim 4, wherein the control circuit comprises a processing unit programmed to determine whether the tissue clamped in the end effector is within the specified thickness range for the removable cartridge based on the thickness data and the model type data.

6. The surgical instrument of claim 5, wherein the control circuit comprises solid state memory, wherein the solid state memory stores thickness range data for one or more cartridge types.

7. The surgical instrument of claim 6, wherein the processing unit is programmed to determine whether the tissue clamped in the end effector is within the specified thickness range for the removable cartridge based on the data communicated to the control circuit by the tissue thickness module by comparing the data indicative of the thickness of the tissue clamped in the end effector to the stored thickness range data for the cartridge type of the removable cartridge in the end effector.

8. The surgical instrument of claim 7, wherein:
the surgical instrument further comprises a drive shaft that drives the moveable working portion;
the electric motor actuates the drive shaft; and
the power source comprises a battery pack that supplies the electrical power to the electric motor.

9. The surgical instrument of claim 8, wherein the tissue thickness module is in wireless communication with the control circuit.

10. The surgical instrument of claim 9, wherein the tissue thickness module is in wireless communication with a visual display unit.

11. The surgical instrument of claim 9, wherein the tissue thickness module is in wireless communication with a remote computer system.

12. The surgical instrument of claim 9, wherein:
the tissue thickness module comprises a first radio module; and
the control circuit comprises a second radio module, wherein the first radio module wirelessly communicates with the second radio module.

13. The surgical instrument of claim 2, wherein the removable cartridge comprises a disposable staple cartridge.

14. The surgical instrument of claim 1, wherein the moveable working portion comprises a cutting instrument.

15. A surgical cutting and fastening instrument comprising:
an end effector, wherein the end effector comprises:
first and second opposing jaw members moveable between open and closed position;
a moveable cutting instrument that severs tissue clamped between the first and second jaw members when the jaw members are in the closed position;
a magnet at a distal end of the first jaw member;
a disposable cartridge in the second jaw member, wherein the disposable cartridge comprises a tissue thickness module that senses thickness of tissue clamped between the first and second jaw members, wherein the tissue thickness module comprises a Hall effect sensor that senses a magnetic field strength from the magnet, wherein the magnetic field strength is indicative of the thickness of the tissue clamped between the first and second jaw members;
a drive shaft that drives the cutting instrument;
an electric motor for actuating the drive shaft;
a power source connected to the motor via at least one switch, wherein the power source is for supplying electric power to the electric motor; and
a control circuit in communication with the tissue thickness module, wherein the control circuit comprises a processing unit programmed to determine whether the tissue clamped in the end effector is within a specified thickness range for the disposable cartridge based on data communicated to the control circuit by the tissue thickness module, wherein the control circuit automatically prevents actuation of the drive shaft when the thickness of the tissue clamped in the end effector is not within the specified thickness range for the disposable cartridge by controlling the at least one switch that connects the power source to the electric motor.

16. The surgical instrument of claim 15, wherein the tissue thickness module communicates the data to the control circuit, the data comprising:
data indicative of the thickness of the tissue clamped in the end effector; and
data indicative of a cartridge type of the disposable cartridge.

17. The surgical instrument of claim 16, wherein the control circuit comprises solid state memory, wherein the solid state memory stores thickness range data for one or more cartridge types.

18. The surgical instrument of claim 17, wherein the processing unit is programmed to determine whether the tissue clamped in the end effector is within the specified thickness range for the disposable cartridge based on the data communicated to the control circuit by the tissue thickness module by comparing the data indicative of the thickness of the tissue clamped in the end effector to the stored thickness range data for the cartridge type of the disposable cartridge in the end effector.

19. The surgical instrument of claim 15, wherein the tissue thickness module is in wireless communication with the control circuit.

20. The surgical instrument of claim 15, wherein the power source comprises a battery.

21. A surgical instrument comprising:
a tissue-clamping end effector that comprises:
first and second opposing jaw members;
a moveable working portion;
a cartridge located in the first jaw member;

a thickness sensor on the cartridge that senses thickness of tissue clamped between the first and second jaw members;

a microcontroller in communication with the thickness sensor, wherein the microcontroller stores data indicative of a cartridge type of the cartridge; and a radio module in communication with the microcontroller;

an electric motor that actuates the moveable working porting of the end effector;

a power source connected to the electric motor via at least one switch, wherein the power source is for supplying electric power to the electric motor; and a control circuit in communication with the radio module, wherein:

the control circuit receives data from the radio module, the data comprising:

data indicative of the thickness of the tissue clamped in the end effector; and the data indicative of the cartridge type of the disposable cartridge the control circuit determines whether the tissue clamped in the end effector is within a specified thickness range for the disposable cartridge based on the data communicated to the control circuit; and the control circuit automatically prevents actuation of the moveable working portion when the thickness of the tissue clamped in the end effector is not within the specified thickness range for the disposable cartridge by controlling the at least one switch that connects the power source to the electric motor.

* * * * *